(12) United States Patent
Reichen et al.

(10) Patent No.: US 11,427,853 B2
(45) Date of Patent: Aug. 30, 2022

(54) SINGLE CELL ANALYSIS

(71) Applicant: HIFIBIO SAS, Paris (FR)

(72) Inventors: Marcel Reichen, Waedenswil (CH);
Arnaud Reitz, Guyancourt (FR);
Bingqing Shen, Chatillon (FR); Sami Ellouze, Chatenay Malabry (FR);
Annabelle Gerard, Palaiseau (FR)

(73) Assignee: HIFIBIO SAS, Paris (FR)

( * ) Notice: Subject to any disclaimer, the term of this patent is extended or adjusted under 35 U.S.C. 154(b) by 231 days.

(21) Appl. No.: 16/494,537

(22) PCT Filed: Mar. 15, 2018

(86) PCT No.: PCT/EP2018/056551
§ 371 (c)(1),
(2) Date: Sep. 16, 2019

(87) PCT Pub. No.: WO2018/167218
PCT Pub. Date: Sep. 20, 2018

(65) Prior Publication Data
US 2020/0199649 A1    Jun. 25, 2020

(30) Foreign Application Priority Data

Mar. 17, 2017 (EP) .................................... 17305297

(51) Int. Cl.
*C12Q 1/6806* (2018.01)
*C12N 15/10* (2006.01)

(52) U.S. Cl.
CPC ....... *C12Q 1/6806* (2013.01); *C12N 15/1075* (2013.01); *C12Q 2521/107* (2013.01); *C12Q 2535/122* (2013.01); *C12Q 2563/159* (2013.01); *C12Q 2563/179* (2013.01); *C12Q 2565/629* (2013.01)

(58) Field of Classification Search
CPC ............ C12Q 1/6806; C12Q 2521/107; C12Q 2535/122; C12Q 2563/159; C12Q 2563/179; C12Q 2565/629; C12N 15/1075
See application file for complete search history.

(56) References Cited

U.S. PATENT DOCUMENTS 10,745,741 B2 * 8/2020 Utharala ................... B01L 7/52

FOREIGN PATENT DOCUMENTS

| CN | 106460033 A | 2/2017 |
|----|-------------|--------|
| CN | 104471077 B | 5/2017 |
| WO | 2016/040476 A1 | 3/2016 |
| WO | WO-2016145409 A1 | 9/2016 |
| WO | WO-2016191533 A1 | 12/2016 |
| WO | WO-2016207441 A1 | 12/2016 |
| WO | 2017/035347 A1 | 3/2017 |

OTHER PUBLICATIONS

International Search Report and Written Opinion for Application No. PCT/EP2018/056551, dated May 25, 2018, 11 pages.
Labanieh, Louai, et al., "Floating Droplet Array: An Ultrahigh-Throughput Device for Droplet Trapping, Real-time Analysis and Recovery", Micromachines, vol. 6, No. 10, pp. 1469-1482 (Jan. 2015).
Shembekar, Nachiket, t al., "Droplet-based microfluidics in drug discovery, transcriptomics and high-throughput molecular genetics", Lab on a Chip, vol. 16, pp. 1314-1331 (Jan. 2016).
Yuan, Jinzhou, et al, "An Automated Microwell Platform for Large-Scale Single Cell RNA-Seq", Scientific Reports, vol. 6, No. 1, (Dec. 1, 2016).

\* cited by examiner

*Primary Examiner* — David C Thomas
(74) *Attorney, Agent, or Firm* — McCarter & English, LLP; Yu Lu; James M. Alburger

(57) ABSTRACT

The present invention concerns processes for barcoding nucleic acids from single cells and processes for genotyping single cells having a phenotype of interest.

5 Claims, 12 Drawing Sheets

SINGLE CELL ANALYSIS

CROSS-REFERENCE TO RELATED APPLICATIONS

This application is a national stage filing under 35 U.S.C. § 371 of International Application No. PCT/EP2018/056551, filed on Mar. 15, 2018, which claims the benefit of and priority to European Patent Application No. 17305297.8, filed on Mar. 17, 2017, the contents of all of which are incorporated by reference herein in their entirety. International Application No. PCT/EP2018/056551 was published under PCT Article 21(2) in English.

FIELD OF THE INVENTION

The present invention concerns processes for barcoding nucleic acids from single cells and processes for genotyping single cells having a phenotype of interest.

BACKGROUND OF THE INVENTION

Methods for analyzing multiple parameters of single cells in populations are of interest in a variety of contexts. In particular, the ability to analyze nucleic acids, optionally in combination with one or more other parameters, on a single-cell basis within a cell population is of broad interest to commercial and academic laboratories. Moreover, it is often necessary for this analysis to be performed in real-time in order to reveal the dynamic behavior of biological and biochemical processes.

Thus, technologies that can isolate, detect, and quantify individual components of a heterogeneous mixture in a highly parallel fashion are needed to meet these challenges. Conventional high-throughput platforms such as high-density microwell plates with robotic dispensing systems have been developed and widely used for high-throughput analysis, such as drug screening. However, they require expensive and bulky robotic machinery and suffer from sample evaporation and comparably large reaction volumes, which can waste precious biological samples or reagents.

Recently, microfabricated devices have emerged as a powerful experimental platform for performing a diverse range of biological and chemical assays in a high-throughput manner. These technologies often permit high-throughput analysis of a complex sample by partitioning a bulk solution into many isolated pico to nanoliter-sized compartments, or microreactors. However, post-analysis retrieval of individual samples is difficult to achieve. Furthermore, mixing of reagents in these devices either requires complex architecture or is often done in bulk before compartmentalization, which may prevent initial reaction products from co-localizing with their initiating target.

One approach is to compartmentalize reactions into discrete micron-sized droplets surrounded by an immiscible carrier fluid. Droplet-based microfluidics provides precise control over mixing of fluids, minimizes waste of precious reagents, and reduces evaporation and adsorption of molecules at the device walls.

White et al. (Proc Natl Acad Sci USA. 2011 Aug. 23; 108(34):13999-4004) describe a microfluidic device capable of performing RT-qPCR measurements of gene expression from hundreds of single cells per run, executing single-cell processing, including cell capture, cell lysis, reverse transcription, and quantitative PCR. However, incited to try smaller reaction volumes, White et al. (Proc Natl Acad Sci USA. 2011 Aug. 23; 108(34):13999-4004) performed 300 parallel RT-qPCR and demonstrated that RT is inhibited in volumes that are smaller than 5 nL in the reaction conditions tested. The researchers thus performed the RT reaction in 67 nL per cell and further claimed that the combination of RT and qPCR in a single reaction precludes large-scale transcriptome analysis and/or unbiased amplification.

Furthermore, a method using a simple axisymmetric flow-focusing device has been described for single cell mRNA capture by DeKosky et al. (Nat Med. 2015 January; 21(1):86-91). The RT and PCR reaction of the method take place in an emulsion. This process has proven to be efficient, yet requiring performing sequential 3 steps process.

Along the same line, Eastburn et al. (Anal Chem. 2013 Aug. 20; 85(16):8016-21) performed RT in small droplet volume, yet in a time consuming 3-4 steps process. They mentioned also RT inhibition in small volume from cell proteinase. To overcome this problem, they treat the cells with proteinase, dilute cell lysate, split drops, and pico-inject RT-PCR reagents.

Rotem et al. (PLoS One. 2015 May 22; 10(5):e0116328) encapsulate oligo in droplet population and fuse them to droplet containing cells while pico-injecting the RT enzymes and buffers. This 3 step process produces ~100 pL droplets allowing encapsulation of 100.000 cells in 3 h. Although this method relies on single cell cDNA labeling, the transcriptomic sequence data comes from an aggregate of multiple phenotypically and genotypically uncorrelated cells.

Macosko et al. (Cell. 2015 May 21; 161(5):1202-14) used droplet-based microfluidics to encapsulate cells together with lysis reagents and barcoded beads to capture mRNA in 1 nL drops. The beads are, however, used off chip to perform the conversion of the mRNA captured on beads into cDNA and they do not load into most of the formed droplet thus precluding analysis of rare cell populations. The third step of the method described by Macosko et al. is then devoted to library preparation and amplification.

The international patent application WO2015/164212 refers to a method for encapsulating and barcoding single cell nucleic acids. WO2015/164212 discloses that RT of mRNA is strongly inhibited in volumes that are smaller than 3 nL (Example 4 of WO2015/164212).

Labanieh et al. 2015 describes a microfluidic process using a microfluidic device to trap, analyse, and recover droplets using buoyancy. However, Labanieh et al. does not specify the analysis of single cell nucleic acids wherein the nucleic acids are reverse transcribed and therefore the genotype of single cells cannot be obtained using this method.

The patent application US2013/0323732 refers to methods and devices for assaying single cells and barcoding single cell cDNA. US2013/0323732 does not disclose a method wherein droplets are fused within a microfluidic chip.

Contrary to this, the inventors succeeded in developing an on chip microfluidic process for barcoding single cell nucleic acids, wherein single cell droplets are captured in individual compartments. The single cell droplets are further fused with droplets providing the reaction mixture for reverse transcription.

As mentioned above, the on chip process developed by the inventors allows accessing the phenotype of single cells. The inventors therefore further developed a process uniquely coupling phenotype information (protein expression level, cellular pathway activation/activity, ion channel/GPCR activities) with genotypic or epigenetic information, thus allowing determining the genotype of a single cell having a phenotype of interest.

The ability to image the array at each step in the process allows obtaining more quantitative data per single cell than with conventional methods and allows generating kinetic data during the phenotypic screen which can be then linked with the genotype of a particular single cell.

This process differs from the so far known prior art, such as Rotem et al., because in Rotem et al., for example, genomic information is obtained by sequencing an aggregate of multiple phenotypically and genotypically uncorrelated cells. Their method therefore does not disclose coupling phenotype information to the genotype of each single cell.

The international patent application WO2016145409 μl discloses a method wherein phenotypes and genotypes of a protein of interest may be correlated. In this method, different to the method of the inventors, a barcode is linked to, for example, a protein of interest or its binding partner, and at the same time to the nucleic acid encoding said protein of interest. The nucleic acids are then reverse transcribed to obtain barcoded cDNA, the barcoded cDNA is then sequenced. The protein of interest is in parallel phenotyped, by breaking the emulsion and performing a phenotypic assay, such as ELISA, or an essay using affinity columns. For the proteins that show the desired phenotype the barcode sequence may then be analyzed by sequencing. The phenotype is then linked to a genotype by matching the barcode of the protein of interest having a phenotype of interest with a cDNA having the same barcode.

However, as it will be understood by the skilled in the art, such a method does not allow to match a whole transcriptome of a single cell with the phenotype of a single cell or to access the genotypes of single cells having a phenotype which is not associated with the presence of one particular protein of interest.

Contrary to this the method of the inventors allows to phenotype, in one step, several single cells, and then to genotype, in parallel, those single cells by pooling their nucleic acids. Afterwards the genomic information is linked to the phenotype of a single cell having a phenotype of interest.

Furthermore, the process of the inventors allows determining any phenotype including a phenotype that is not necessarily associated with the presence of a single protein of interest but which might be associated with a change of activity of, for example certain pathways, and which results in any phenotype that might be determined using an assay, for example, antibody secretion rate, ion channel activity, GPCR activations, a change the Redox potential of a cell.

SUMMARY OF THE INVENTION

A first aspect of the present invention is directed to a process for genotyping single cells having a phenotype of interest comprising:
  providing a plurality of reservoirs, and
    a) for a plurality of reservoirs, providing, for each reservoir, at least one barcode sequence and at least one dye, wherein the at least one barcode sequence is associated with the color and the concentration of said at least one dye, and taking an image of the array thereby mapping the color and the intensity of the at least one dye for each reservoir; and
    b) for a plurality of reservoirs, providing, for each reservoir, at least one single cell and performing for each reservoir a phenotypic assay on said at least one single cell, and taking an image thereby mapping the phenotype of said at least one single cell for each reservoir;
  wherein step a) is performed before step b) or step b) is performed before step a); then
    c) for a plurality of reservoirs, linking, for each reservoir, the phenotype of a single cell obtained in step b) to the color and the intensity of the at least one dye obtained in step a); and
  for a plurality of reservoirs, reverse transcribing, for each reservoir, nucleic acids of said at least one single cell, to obtain single cell cDNA barcoded with said at least one barcode sequence which is associated with the color and concentration of the at least one dye; and
  linking the genotype with the phenotype of said at least one single cell.

A second aspect of the present invention is directed to a microfluidic process for barcoding single cell nucleic acids, said method comprising:
  providing a microfluidic device comprising a chip comprising at least one microfluidic channel and a plurality of reservoirs,
  injecting into the inlet of the microfluidic channel a carrier fluid comprising a plurality of droplets of a first type dispersed in the carrier fluid, wherein the droplets of the first type are either single cell droplets or RT droplets, wherein at least some of the RT droplets comprise a reverse transcriptase and at least one oligonucleotide, and wherein at least some of the single cell droplets comprise one single cell, wherein said single cell comprises single cell nucleic acids,
  for a plurality of reservoirs, a first migration step, wherein at least one droplet of the first type among the plurality of droplets is moved into one reservoir of said plurality of reservoirs by buoyancy,
  injecting into the inlet of the microfluidic channel, a carrier fluid comprising a plurality of droplets of a second type dispersed in the carrier fluid, wherein the droplets of the second type are either single cell droplets or RT droplets, and wherein the droplets of the second type are RT droplets when the droplets of the first type are single cell droplets or the droplets of the second type are single cell droplets when the droplets of the first type are RT droplets,
  for a plurality of reservoirs, a second migration step, wherein, at least one part of at least one droplet of the second type enters into one reservoir of said plurality of reservoirs,
  for a plurality of reservoirs, fusing, in or at the edge of each reservoir, said at least one droplet of the first type with said at least one droplet of the second type, thereby resulting in a fused droplet,
  and further comprising the steps of:
    a) hybridizing, for each fused droplet, the at least some of the single cell nucleic acids with the at least one oligonucleotide in said fused droplet,
    b) reverse transcribing, in each fused droplet, at least some of the single cell nucleic acids present in said fused droplet, thereby resulting in single cell cDNA, and
    c) attaching at least one barcode sequence to the single cell cDNA obtained in step b), wherein said at least one barcode sequence encodes the identity of said single cell, or
  further comprising the steps of:
    a) hybridizing, for each fused droplet, at least some of single cell nucleic acids from at least one cell with the at least one oligonucleotide in said fused droplet, wherein said at least one oligonucleotide comprises at least one barcode sequence, b) reverse transcribing, in each fused droplet, at least some of the single cell nucleic acids present in said fused droplet, thereby resulting in barcoded single cell cDNA, wherein said at least one barcode sequence encodes the identity of said single cell.

DETAILED DESCRIPTION OF THE INVENTION

Definitions

Figure 1:
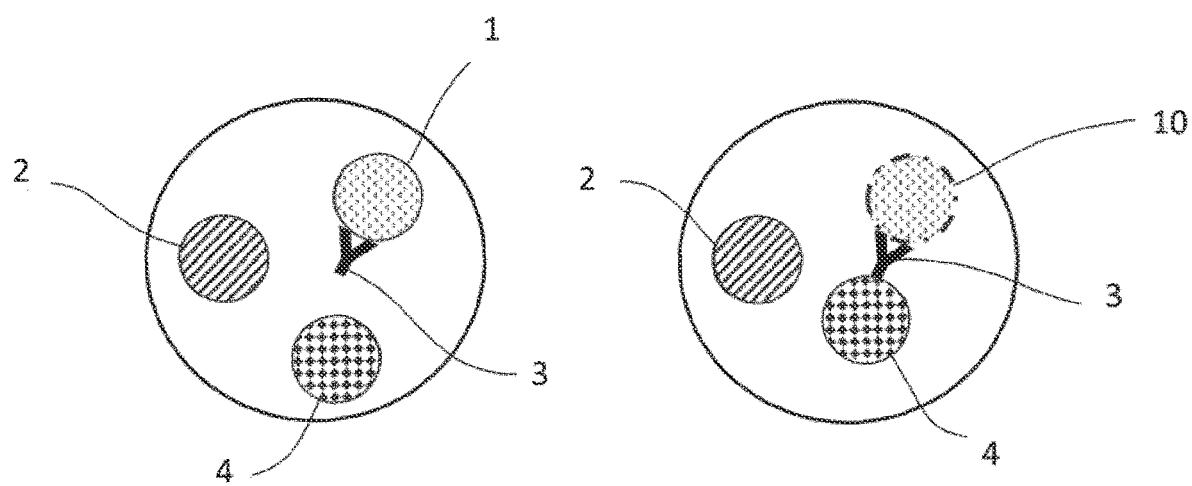
FIG. 1 shows a single cell droplet based phenotype assay for identification of Antibody Dependent Cell Mediated Cytotoxicity (ADCC). The IgG producing cell (2) secrete an antibody targeting a reporter cell expressing a membrane protein (1). After antibody binding on the targeted cell (3), the killing cells (4) are recruited through the cell Fc receptor, which will induce cytotoxic activity (10) mediated through the binding of antibody secreted by (2). In some application the killing cells are isolated from PBMC5 or are cell lines know with cytotoxic mediated activity.

Unless otherwise defined, scientific and technical terms used in connection with the disclosure shall have the meanings that are commonly understood by those of ordinary skill in the art.

Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well-known and commonly used in the art.

By "microfluidic", it is generally meant that the dimensions of the passages in which the fluid circulates are smaller than one millimeter and are comprised, for example, from 1 µm and 1 mm.

"Microfluidic processes" generally refer to processes wherein small amounts of fluids ($10^{-4}$ to $10^{-18}$ liters) are manipulated using microfluidic channels with dimension smaller than one millimeter. Those microfluidic channels are usually contained within a microfluidic device, more particularly within the microfluidic chip of a microfluidic device. Microfluidic devices that are used in context of the present invention are further described herein below in the section "Microfluidic devices".

The "process" of the invention may also be referred to as a method.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The term "nucleic acid" as herein used generally refers to at least one molecule or strand of DNA, RNA, miRNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the term "oligonucleotide".

"RNA" herein refers to, but is not limited to, functional RNA, such as mRNA, tRNA, rRNA, catalytic RNA, siRNA, miRNA and antisense RNA. In one preferred embodiment, RNA refers to mRNA.

As it will be understood by those skilled in the art, the depiction of a single strand also defines the sequence of the complementary strand. Thus, a nucleic acid also encompasses the complementary strand of a depicted single strand. The term nucleic acid thus encompasses complementary DNA. As it will also be appreciated by those skilled in the art, many variants of a nucleic acid may be used for the same purpose as a given nucleic acid. Thus, a nucleic acid also encompasses substantially identical nucleic acids and complements thereof. As it will also be understood by those skilled in the art, a single strand nucleic acid, such as, a primer, may hybridize to the target sequence under hybridization conditions, preferably stringent hybridization conditions. Thus, a nucleic acid also encompasses a primer that hybridizes under hybridization conditions to a target sequence.

The term "oligonucleotide" refers to at least one molecule of about 3 to about 500 nucleobases in length. For example, the oligonucleotide may have a length of at least 3 nucleobases, at least 10 nucleobases, at least 30 nucleobases, at least 50 nucleobases, at least 100 nucleobases, at least 300 nucleobases, or at least 400 nucleobases. In some cases, the oligonucleotide may have a length of no more than 500 nucleobases, no more than 300 nucleobases, no more than 100 nucleobases, no more than 50 nucleobases, etc. Combinations of any of these are also possible, e.g., the length of the oligonucleotide may be between 3 and 300 nucleobases, preferably 3 and 200 nucleobases, more preferably 3 to 100 nucleobases.

These definitions refer to at least one single-stranded molecule, but in some embodiments encompass also at least one additional strand that is partially, substantially or fully complementary to the at least one single-stranded molecule. Accordingly, in some embodiments said definitions refer to double stranded molecules.

Thus, in some embodiments, a nucleic acid refers to at least one double-stranded molecule that comprises one or more complementary strand(s) or "complement(s)" of a particular sequence comprising a strand of the molecule.

"Gene" as used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA and antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

The term "stringent condition" or "high stringency condition" as used herein corresponds to conditions that are suitable to produce binding pairs between nucleic acids having a determined level of complementarity, while being unsuitable to the formation of binding pairs between nucleic acids displaying a complementarity inferior to said determined level. Stringent conditions are the combination of both hybridization and wash conditions and are sequence dependent. These conditions may be modified according to methods known from those skilled in the art (Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, high stringency conditions are selected to be about 5° C. lower than the thermal melting point (Tm), preferably at a temperature close to the Tm of perfectly base-paired duplexes (Andersen, Nucleic acid Hybridization, Springer, 1999, p. 54).

Hybridization procedures are well known in the art and are described for example in Ausubel, F.M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

High stringency conditions typically involve hybridizing at about 50° C. to about 68° C., wherein said temperature typically corresponds to the highest melting temperature TM of the nucleic acid to be hybridized with a target sequence, in 5×SSC/5×Denhardt's solution/1.0% SDS and washing in 0.2×SSC/0.1% SDS at about 60° C. to about 68° C. For instance, in context with the present invention the primer sequence comprised in the at least one oligonucleotide typically hybridizes with a complementary nucleic acid, for example a complementary RNA sequence, at about 50° C. to about 68° C. in, typically, a reservoir, or a droplet or a plurality of droplets, such as the so-called fused droplet or the plurality of fused droplets. Accordingly, in one example, said fused droplet or said reservoir further comprises a reverse transcriptase composition and, optionally, a lysis composition, wherein the reverse transcriptase composition is defined herein below in the section "reverse transcription" and the lysis composition is defined herein below in the section "cell lysis".

The term "antibody" refers to immunoglobulin molecules and immunologically active portions of immunoglobulin molecules, i.e., molecules that contain an antigen binding site which immunospecifically binds an antigen. As such, the term antibody encompasses not only whole antibody molecules, but also antibody fragments as well as variants of antibodies, including derivatives such as humanized antibodies. In conventional antibodies, two heavy chains are linked to each other by disulfide bonds and each heavy chain is linked to a light chain by a disulfide bond. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding affinity and specificity of the natural Fv region of a native immunoglobulin binding-site. The light and heavy chains of an immunoglobulin each have three CDRs, designated L-CDR1, L-CDR2, L-CDR3 and H-CDR1, H-CDR2, H-CDR3, respectively. Therefore, an antigen-binding site includes six CDRs, comprising the CDR set from each of a heavy and a light chain V region. Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al. (Sequences of Proteins of Immunological Interest (National Institutes of Health, Bethesda, Md., 1991).

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments. The term antibody therefore further denotes single chain antibodies, for instance Camelidae antibodies, or nanobodies or VHH.

The term "T-cell receptor" herein refers to an antigen-recognition molecule present on the surface of T cells (i.e., T lymphocytes). This definition expressly includes the understanding of the term as known in the art, and includes, for example, a receptor that comprises or consists of a disulfide-linked heterodimer of the highly variable alpha or beta chains expressed at the cell membrane as a complex with the invariant CD3 chains, or a receptor that comprises or consists of variable gamma and delta chains expressed at the cell membrane as a complex with CD3 on a subset of T-cells.

"Antibody genes" and "T-cell receptor genes" undergo a unique mechanism of genetic recombination, called V(D)J recombination, that occurs only in developing lymphocytes during the early stages of T and B cell maturation. It involves somatic recombination, and results in the highly diverse repertoire of antibodies/immunoglobulins (Igs) and T cell receptors (TCRs) found on B cells and T cells, respectively.

The term "plurality" herein refers to any number which is more than 1 of the object concerned, such as more than 500, more than 1000, more than 2000, more than 5000, more than 100000, such as 1 to 100000, for example 1 to 10000, 1 to 10000, 10 to 1000, 50 to 1000, 100 to 1000, 10 to 500 of the object concerned.

Microfluidic Devices

The microfluidic processes of the present inventions are performed in microfluidic devices comprising a chip.

"Microfluidic chips" generally refer to a set of microchannels made by milling, etching, ablation or molding into a material (glass, silicon or polymer such as PDMS, PMMA or COC). A microfluidic chip usually comprises a substrate and a support, defining together at least one channel.

In some embodiments of the present invention, the microfluidic device used in context of the present inventions comprises a chip comprising a plurality of reservoirs.

In some embodiments of the present invention, the microfluidic device used in context of the present inventions comprises a chip comprising at least one microfluidic channel and a plurality of reservoirs.

In related embodiments, the at least one microfluidic channel extends in a longitudinal direction (X) between an inlet and an outlet.

In related embodiments, each reservoir of the plurality of reservoirs extends along an elevation direction (Z) forming a non-zero angle with the longitudinal direction (X), and each reservoir opens into the at least one channel extending in a longitudinal direction (X).

Accordingly, in some embodiments, the microfluidic device comprises a chip comprising:
at least one microfluidic channel, extending in a longitudinal direction (X) between an inlet and an outlet,
a plurality of reservoirs, wherein each reservoir is extending along an elevation direction (Z) forming a non-zero angle with the longitudinal direction (X), and each reservoir opening into the at least one channel.

In some embodiments, "at least one microfluidic channel" herein refers to at least 1 to 100, 1 to 80, 1 to 50, 1 to 40, 1 to 30, 1 to 20, 1 to 10, such as 1 to 6, 1 to 4, 1 to 3 channels.

In some embodiments, the non-zero angle formed between the elevation direction (Z) and the longitudinal direction (X) is from 85° to 95°, preferably 90°.

The inlet of the channel is usually used to inject at least one fluid and the outlet of the channel is usually used to collect at least one fluid. The channel is usually intended to allow flowing of the at least one fluid along the main direction from the inlet toward the outlet.

The inlet of the channel may be connected with at least one reservoir, such as one to five, preferably one to four, more preferably, one to three, such as one, two or three reservoirs of a fluid intended to flow in the channel.

The outlet of the channel may be connected to at least one reservoir, preferably one or two reservoirs, to collect the fluid coming from the channel.

In some embodiments, the chip is a drop array, more particularly, a floating drop array.

In some embodiments, said microfluidic device further comprises at least one injection device to control the flow rate of the at least one fluid.

"At least one fluid" herein may refer to at least one, at least two, at least three, at least four, at least five or more than five fluids. The "at least one fluid" injected at the inlet and the "at least one fluid" collected at the outlet may be the same fluid or different fluids.

The injection device may comprise a pressure controller or a syringe driver.

In some embodiments, the at least one fluid at the inlet refers to one, two, three or four fluids, for example three fluids.

Accordingly, in one example, one fluid contains, for example, droplets of a first type, one second fluid contains, for example, droplets of a second type and a third fluid is to remove a plurality of either the first type or the second type of droplets and to clear out the chamber. The droplets of a first type and a second type are as defined herein below in context of the processes of the invention. According to said example, said microfluidic device further comprises an injection device to control the flow rate of said three fluids.

In some embodiments, the device comprises at least one electric system, preferably one electric system, adapted to induce an electric field in a specific area of the chip. The at least one electric system may comprise a generator, an anode and a cathode.

In some embodiments, the microfluidic device in context of the invention is used in a device assembly.

Said device assembly might further comprise a cell sorter or a unit for producing droplets, such as droplets of the first type or the second type, such as, single cell droplets or RT droplets as further defined herein below.

Accordingly, in one alternative embodiment, the chip might comprise a unit for producing droplets of the first type or the second type such as single cell droplets or RT droplets as further defined herein below.

Those droplets are then injected via the inlet into the at least one microfluidic channel.

"A plurality of reservoirs" herein refers to any number of reservoirs. The number of reservoirs and thus a plurality of reservoirs preferably refers to from 1 to 100000 reservoirs, for example 1 to 10000 reservoirs, such as 10 to 8000, 10 to 7000, 10 to 6000, 10 to 5000, 10 to 4000, 10 to 3000, 10 to 2000, 10 to 1000, for example 1000 to 10000, 1000 to 9000, 2000 to 8000, 3000 to 7000, 4000 to 6000, for example 4500 to 5500.

In context of the invention, reference may be made to one reservoir of the microfluidic device. However, the skilled in the art understands that processes described for one reservoir apply in parallel to a plurality of reservoirs present in the chip used.

In some embodiment the reservoirs of the chip have the form of a cylinder. In some embodiments, the size of the reservoirs of the plurality of reservoirs is homogenous.

It will be understood by the skilled in the art that the microfluidic device, more particularly the chip of the microfluidic device, may be characterized by its geometric parameters, such as, the diameter of one reservoir of the plurality of reservoirs, $d_{reservoir}$, depth of the reservoir, $h_{reservoir}$, height of the injection channel, $h_{channel}$, width of the injection channel, $w_{channel}$, and the space between the individual reservoirs of the plurality of reservoirs, x.

Droplets

A "droplet" generally refers to a measure of volume. A "droplet" refers in context of the present invention, to an isolated portion of a first fluid that is surrounded by a second fluid. It is to be noted that a droplet is not necessarily spherical, but may assume other shapes as well depending, for example, on the external environment.

The term "droplets" used in context of the processes of the invention includes droplets of a first type, droplets of a second type, such as single cell droplets or RT droplets, and fused droplets, or a plurality of said droplets.

Methods to prepare and inject droplets are known to the skilled in the art and are further explained herein below in the section "preparation of droplets". With regards to the preparation of droplets, it will be understood by the skilled in the art that the size of the droplets follows a probability distribution, such as a Gaussian distribution. It will be further understood that the parameters used for the preparation of microfluidic droplets can be chosen in order to obtain a plurality of microfluidic droplets having a specific volume.

In some embodiments, the droplets in context of the processes of the invention, in particular, the droplets of the first type or the droplets of the second type are preferably, substantially, monodisperse.

"Monodisperse" herein refers to droplets having substantially the same shape and/or size.

As mentioned herein above, and as known by the skilled in the art, the droplets follow a shape and size distribution. Accordingly, the droplets may have a homogenous distribution of cross-sectional diameters, i.e., the droplets may have a distribution of diameters or volumes such that no more than about 5%, no more than about 2%, or no more than about 1% of the droplets have a diameter or volume less than about 90% (or less than about 95%, or less than about 99%) and/or greater than about 110% (or greater than about 105%, or greater than about 101%) of the overall average diameter or volume of the plurality of droplets. Some techniques for producing homogenous distributions of cross-sectional diameters of droplets are disclosed in International Patent Application No. PCT/US2004/010903, filed Apr. 9, 2004, entitled "Formation and Control of Fluidic Species," by Link et al., published as WO 2004/091763 on Oct. 28, 2004, incorporated herein by reference. It will be understood by the skilled in the art, when reference is made herein to a volume or a size of a droplet, this volume or size refers to the average volume or size of the plurality of droplets. Those of ordinary skill in the art will be able to determine the average diameter of a population of droplets, for example, using laser light scattering or other known techniques. The droplets formed in context of the invention can be spherical, or non-spherical in certain cases. The diameter of a droplet, in particular a non-spherical droplet, may be taken as the diameter of a perfect mathematical sphere having the same volume as the non-spherical droplet.

The "droplet" or "the plurality of droplets" such as the "plurality of RT droplets" or the "plurality of single cell droplets" have an average volume of less than 5 nL, such as less than 4 nL, less than 3 nL, preferably less than 3 nL. In some embodiments, said plurality of microfluidic droplets have an average volume of less than 3 nL, less than 2.5 nL, less than 2 nL, less than 1.5 nL, less than 1 nL, less than 0.5 nL, for example 0.1 nL to 3 nL, 0.5 nL to 3 nL, 1 nL to 3 nL, typically, 10 pL, 20 pL, 30 pL, 50 pL, 0.1 nL, 0.5 nL, 1 nL, 1.2 nL, 1.4 nL, 1.6 nL, 1.8 nL, 2.0 nL, 2.2 nL, 2.4 nL, 2.6 nL, 2.8 nL, 3 nL.

In some embodiments, the droplets of the plurality of microfluidic droplets have an average volume of 1 pL to 5000 pL, 10 pL to 5000 pL or 10 pL to 3000 pL.

In some embodiments, the droplets of the plurality of microfluidic droplets have an average volume equal to or less than 1 nL.

Accordingly, the "fused droplet" or "the plurality of fused droplets" have an average volume of less than 10 nL. In some embodiments, said plurality of fused droplets have an average volume of less than 9 nL, less than 8 nL, less than 7 nL, less than 6 nL, less than 5 nL, less than 4 nL, less than 3 nL, less than 2 nL, less than 1 nL, less than 0.5 nL, for example 0.1 nL to 10 nL, 0.1 nL to 8 nL, 0.1 nL to 6 nL, 0.1 nL to 5 nL, such as 0.1 nL to 3 nL, 0.5 nL to 5 nL, 0.5 nL to 3 nL, 1 nL to 3 nL, typically, 0.1 nL, 0.5 nL, 1 nL, 1.2 nL, 1.4 nL, 1.6 nL, 1.8 nL, 2.0 nL, 2.2 nL, 2.4 nL, 2.6 nL, 2.8 nL, 3 nL, 4 nL or 5 nL, such as 11 pL to 8000 pL.

In some embodiments, the plurality of droplets of the first type or the second type, preferably of the first type, have an average diameter that is smaller than the height of the injection channel ($h_{channel}$).

In some embodiments, the plurality of droplets of the first type or the second type, preferably of the first type, have an average diameter that is 30% to 100% of the height of the injection channel ($h_{channel}$), such as 60% to 100%, 70% to 100%; 80% to 100%, 90% to 100%, 92% to 98%, 94% to 98%, for example 95% of the height of the injection channel ($h_{channel}$).

As it will be understood by the skilled in the art, in particular, the plurality of droplets of the first type have an average diameter that is 30% to 100% of the height of the injection channel ($h_{channel}$) as described above, when at least one droplet of the first type among the plurality of droplets moves into one reservoir of said plurality of reservoirs by buoyancy.

In some embodiments, the plurality of droplets of the first type or the second type, preferably of the first type, have an average diameter that is 60% to 95%, such as 70% to 90%, 75% to 85%, or 75% to 80% of the diameter of the reservoir ($d_{reservoir}$), preferably 75 to 80%.

In some embodiments, the plurality of droplets of the second type have an average diameter that is bigger than the height of the injection channel ($h_{channel}$), such as an average diameter that is 100% to 250%, 120% to 250%, 150% to 250%, 200 to 250 preferably 200% to 250%.

As it will be understood by the skilled in the art, the plurality of droplets of the second type have an average diameter that is bigger than the height of the injection channel ($h_{channel}$) as described herein above, when, in the migration step, at least one part of one droplet of the second type enters into one reservoir of said plurality of reservoirs due to the difference in surface energy.

In some embodiments, the plurality of droplets of the second type have an average diameter that is smaller or is as large as the droplets of the first type.

In some preferred embodiments, the plurality of droplets of the first type or second type, preferably the plurality of droplets of the first type, have an average volume from 1 pL to 5000 pL, typically 1 pL to 4000 pL, 1 pL to 3000 pL, such as 1 pL to 500 pL, 1 pL to 400 pL, 1 pL to 300 pL, 1 pL to 200 pL or 1 pL to 100 pL, preferably 1 pL to 100 pL.

In some embodiment, the plurality of droplets of the second type have an average volume that is equal to or an average volume that is higher than the average volume of the plurality of droplets of the first type.

In some preferred embodiments, the plurality of droplets of the second type have an average volume from 10 pL to 5000 pL, 10 pL to 4000 pL, 10 pL to 3000 pL, such as 100 pL to 4000 pL, 100 pL to 3000 pL, 100 pL to 2000 pL or 100 to 1000 pL, preferably, 100 pL to 1000 pL.

In some embodiments, the plurality of droplets of the second type have an average diameter that is 100% to 250%, such as 150% to 250%, 170% to 230%, 180% to 220%, 190% to 210% of the depth of the reservoir ($h_{reservoir}$), for example 200% of the depth of the reservoir ($h_{reservoir}$).

In some embodiments, the plurality of droplets of the second type have an average diameter that is 70% to 130% of the diameter of the reservoir ($d_{reservoir}$), such as 80% to 120%, 90% to 120%, 100% to 120%, 95% to 115%, 95% to 110% of the diameter of the reservoir, preferably 100 to 120% of the diameter of the reservoir ($d_{reservoir}$).

In some embodiments, the plurality of droplets of the second type have an average diameter that is bigger than the diameter of the reservoir ($d_{reservoir}$), when the droplet of the second type enters partly into a reservoir.

In context of the present invention, the microfluidic droplet or plurality of microfluidic droplets comprises an aqueous composition.

The "aqueous composition" in context of the invention is, in case of single cell droplets, typically adapted to the cells used and typically comprises a buffered solution as defined herein below. The aqueous composition, in case of RT droplets, may further comprise for example a reverse transcriptase, a reverse transcription composition and/or a lysis composition.

Preparation of the Droplets

In context of the processes of the invention, in one step, a carrier fluid comprising a plurality of droplets of a first type and, in another step, a carrier fluid comprising a plurality of droplets of a second type are injected into the inlet of the at least one microfluidic channel, preferably one microfluidic channel.

The droplets of the first type are either single cell droplets or RT droplets, features of those droplets are further defined herein below and in the sections "microfluidic process for barcoding single cell droplets", "single cell" and "reverse transcription", respectively, wherein the droplets of the second type are RT droplets when the droplets of the first type are single cell droplets or the droplets of the second type are single cell droplets when the droplets of the first type are RT droplets.

Those of ordinary skill in the art will be aware of techniques for preparing microfluidic droplets. Techniques for encapsulating cells within microfluidic droplets are described for example in U.S. Pat. Nos. 7,708,949, 8,337, 778, 8,765,485, or Int. Pat. Apl. Pub. Nos. WO 2004/091763 and WO 2006/096571, PCT/EP2016/080341 each incorporated herein by reference. Techniques for preparing RT droplets comprising a reverse transcriptase and at least one oligonucleotide can be easily derived by the skilled in the art from the same disclosures, for example PCT/EP2016/080341.

In one example, single cell droplets or RT droplets are prepared prior to injection in a separate microfluidic device. In this example, single cell droplets or RT droplets are typically prepared in a microfluidic device having one inlet for a droplet carrier oil (carrier fluid), and additional inlets for components of the droplet aqueous phase. For the carrier oil, typically, fluorinated oil (e.g. HFE-7500) containing, for example, 0.75% (w/w) surfactant (PFPE-PEG-PFPE triblock copolymer containing two perfluoropolyether blocks (PFPE) and one poly(ethylene)glycol (PEG) block) is typically used. The surfactant is typically used to prevent droplets from coalescing, and the amount may be adjusted, for instance, based on the physicochemical properties of the surfactant used. The carrier oil used for emulsification is not limited to fluorinated liquids and alternative fluids such as fluids based on hydrocarbons (e.g. mineral oil, hexane, etc.), silicon oil and other type of oils can be employed successfully.

For single cell droplet preparation one inlet for droplet carrier oil and, usually, one additional inlet is used for delivering a suspension of dissociated cells.

For RT droplet preparation, in one example, one inlet for a droplet carrier oil and, typically, two additional inlets are used, delivering (1) a reverse transcriptase and (2) the at least one oligonucleotide.

In some embodiments, for RT droplet preparation, for example in context of the processes of the invention, the RT droplets may be fused with other droplets comprising further ingredients, for example, at least one barcode sequence and at least one dye. Methods to fuse flowing droplets are known to the skilled in the art and for example described in WO2010128157 A1.

As it will be understood by the skilled in the art, for example, in case of single cell droplets, the number of cells encapsulated in one droplet and the size of the droplets follows a probability distribution, for example a Poisson or Gaussian distribution, and depends on concentration of the cells, the geometry of the main channel, the injection parameters of the cell suspension and the carrier fluid.

Accordingly, the parameters can be adapted to obtain droplets with either 1 or 0 cells in it, thus avoiding droplets containing several cells.

Accordingly, in context of the invention at least some of the single cell droplets comprise one single cell.

Cells in context of the present invention comprise nucleic acids, it will be therefore understood by the skilled in the art that the single cell droplets in context of the invention comprising single cells thus comprise single cell nucleic acids.

Similar to the preparation of the single cell droplets, it will be understood by the skilled in the art, that in case of RT droplets, the encapsulation of a reverse transcriptase and at least one oligonucleotides follows as well a probability distribution, for example a Poisson or Gaussian distribution, and depends on the concentration of the reverse transcriptase, the concentration of the at least one oligonucleotide, the geometry of the main channel, the injection parameters of the reverse transcriptase, the at least one oligonucleotides and the carrier fluid. Furthermore, in same embodiments, the at least one oligonucleotide comprised in the RT droplets is bound to at least one particle of a first type.

Accordingly, the number of particles of a first type encapsulated in one droplet follows as well a probability distribution, for example a Poisson distribution, and depends on concentration of the particles, the geometry of the main channel, the injection parameters of the particle suspension and the carrier fluid.

Accordingly, the parameters can be adapted to obtain droplets with 0, 1 or 2 particles in it. Accordingly, in some embodiment, at least some of the RT droplets comprise, preferably, one particle of the first type.

The "carrier fluid" is immiscible with aqueous solution of the droplets.

"Carrier fluids" used for the preparation of droplets are known to the skilled in the art and are usually fluorinated oils.

Accordingly, in some embodiments the carrier fluid is fluorinated oil, such as HFE-7500.

Furthermore, in order to prevent droplets from coalescing, the carrier fluid may further comprise a surfactant.

Accordingly, in some embodiments, the carrier fluid further comprises a surfactant.

Surfactants are usually present at 0.1% to 10%, such as 0.1% to 1% or 1% to 10%, 2%, depending on the physicochemical properties of the surfactant. In one example, the carrier fluid comprises 1.5%, 1% or 0.75% (v/v) surfactant, such as PFPE-PEG-PFPE tri-block copolymer containing two perfluoropolyether blocks (PFPE) and one poly(ethylene)glycol (PEG) block.

The surfactant is preferably highly soluble in fluorinated fluids and nearly insoluble in the aqueous phase.

However, since the RT and single cell droplets are fused in a later step the choice and concentration of the surfactant used for the preparation of the droplets preferably does not prevent fusion of said droplets.

Single Cell

As described herein above in the section "preparation of the droplets" encapsulation conditions (conditions to prepare single cell droplets) are preferably chosen in a way that single cell droplets contain 0 or 1 cell. To increase the percentage of droplets containing single cells, the plurality of single cell droplets might be screened and sorted prior to the step of injecting the plurality of single cell droplets.

Furthermore, in some embodiments, said plurality of single cell droplets may be screened for a phenotype of interest prior to injecting the plurality of single cells droplets.

According to alternative embodiments, said plurality of single cell droplets may be screened for a first and/or a second phenotype of interest after injecting the plurality of single cells droplets Example of phenotype of interest is the detection of a biological response. Among these, detection of an immune response can be monitored by detecting ADCC (Antibody-Dependent Cell-Mediated Cytotoxicity) (3) induced by secretion of antigen-specific antibody (see FIG. 1).

Figure 2:
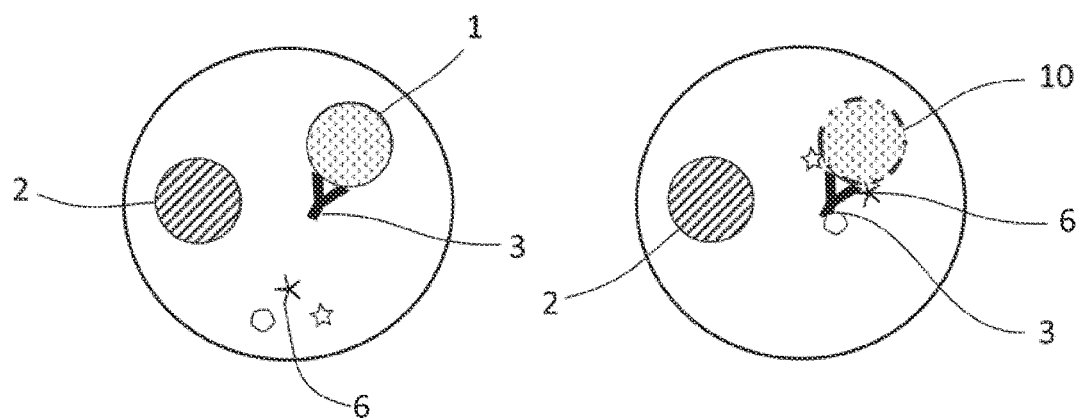
FIG. 2 shows a single cell droplet based phenotype assay for identification of Complement Dependent Cytotoxicity (CDC) antibody. The IgG producing cell (2) secretes an antibody targeting a reporter cell expressing a membrane protein (1). After antibody binding on the targeted cell (3), the complement molecules (6) bind to the antibody inducing the cell lysis (10).

Among biological events, detection of an immune response can be monitored by detecting Complement Dependent Cytotoxicity (CDC) (6) induced by secretion of antigen-specific antibody (see FIG. 2).

Figure 3:
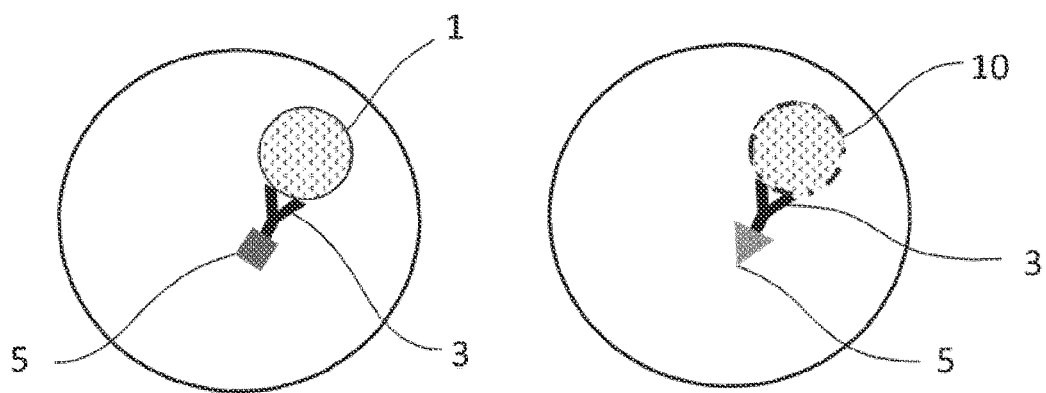
FIG. 3 shows a single cell droplet based phenotype assay for identification of Antibody Drug Conjugate (ADC) (3) candidates inducing cell lysis, apoptosis, internalization, necrosis. A drug coupled antibodies (5) are introduced in different emulsions, one drug per emulsion. After the binding of the antibody (3), and in case of efficient drug activity, the target cell is, in the given example, lysed (10).

Among biological events, detection of a drug effect can be monitored by detecting ADC (Antibody Drug Conjuguate) induced by secretion of antigen-specific antibody (see FIG. 3).

Figure 4:
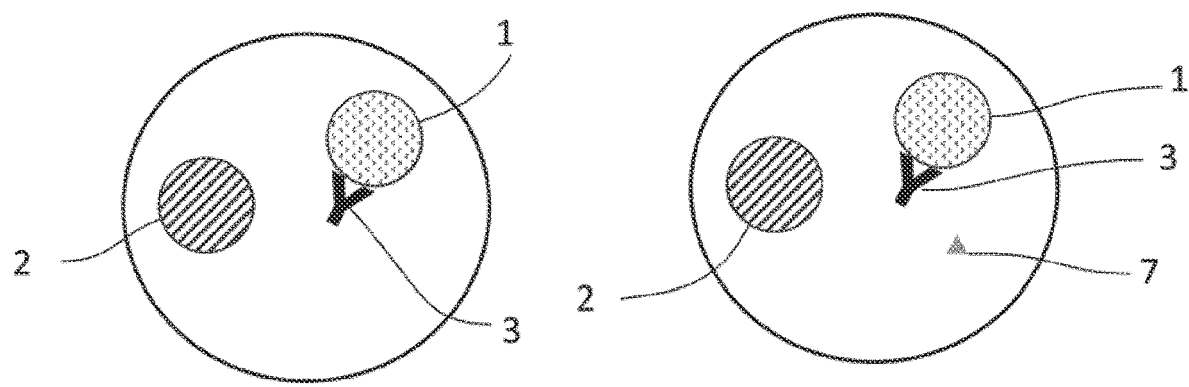
FIG. 4 shows a single cell droplet based phenotype assay for identification of Agonistic/Antagonistic antibody (3). The IgG producing cell (2) secrete an antibody targeting a reporter cell expressing a membrane protein (1). After antibody binding on the targeted cell (1), several pathways are activated or inhibited resulting in physiological modifications. According to the cells and receptor properties, those modifications might be used as single or multiple functional assay in droplet. Differently, an antagonistic antibody (3) would compete with a ligand in the same droplet (7). The readout would then be the blocking of the agonist activity.

Among biological event, is included detection of drug function like agonistic/antagonistic antibody induced by secretion of antigen-specific antibody (see FIG. 4, 5).

Figure 6:
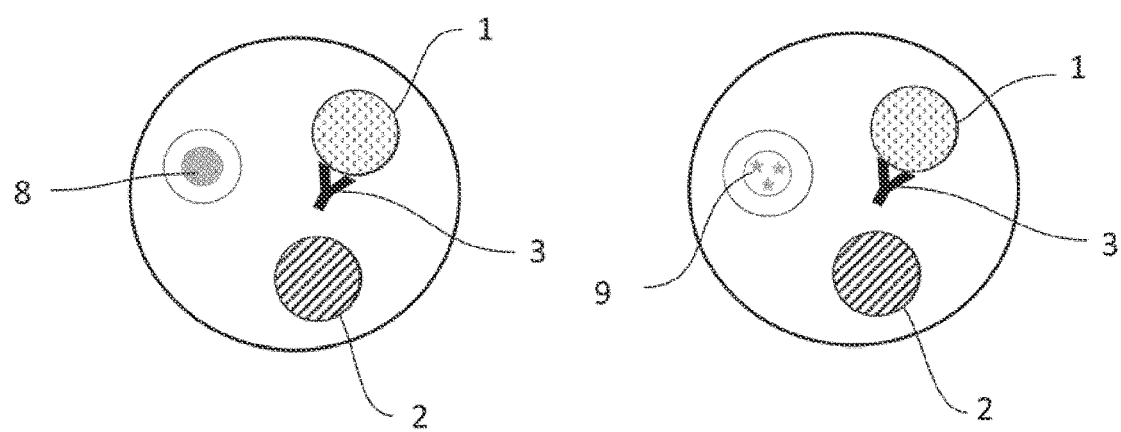
FIG. 6 shows a single cell droplet-based phenotype assay for identification of antagonistic/blocking antibody (3). The IgG producing cell (2) secretes an antibody (3) targeting a reporter cell expressing a membrane protein (1). After antibody binding on the targeted cell (1), a ligand or agonist is progressively released by a particle constituted of a core and a shell (8). The particle can release the ligand in a similar kinetic of antibody production allowing a competition assay in the said droplet. The particle can be constituted by cell growing gel and can generate a gradient of ligand allowing a reporter cell migration inside the gel, commonly called cell mobility assay (9).

Among biological event, is included detection of drug function like performing a competition assay (see FIG. 6).

Among biological event, is included detection of drug function like detection of cell mobility of a reporter cells mediated by the secretion of antibody (see FIG. 6). Such assay can be used to track the modification of behavior of a reporter cell inside the said droplet. A target cell (1) expressing the antigen of interest and loaded with a detectable label that is not released would be co-encapsulated with a IgG producing cell (2) and particles, as single cell droplet. The droplets would be incubated in conditions allowing antibody secretion. The secreted specific antibody would re-localize on the target cell. Meanwhile, a ligand/agonist is diffusing from the particle at similar kinetic than the IgG production and create a gradient of ligand. The reporter cell would migrate inside the particle in function of the ligand concentration (9). In case of blocking antibody (3), the reporter cell progression is altered. The migration can then be used for assessing the blocking/neutralising activity of and antibody.

Accordingly, in some embodiment the single cell droplets are screened and sorted prior to injecting a plurality of single cell droplets.

Microfluidic cell sorting techniques are known to the skilled in the art and described, for example, Wyatt Schields, C. et al. (Lab Chip. 2015 Feb. 16; 15(5): 1230-1249).

Examples of microfluidic cell sorting techniques include, but are not limited to, electrophoresis, dielectrophoresis (DEP), electroosmotic flow, acoustophoresis, optical manipulmation, mechanical systems, magnetophoresis, electrokinetic mechanisms, optical tweezers and passive cell sorting. Some methods might also combine several of these techniques.

Passive cell sorting herein refers to methods relying on inherent differences and sort cells using inertial forces, hydrodynamic spreading, deterministic lateral displacement, filtration, transient cellular adhesion, and cellular immobilization.

In a preferred embodiment, single cell droplets are sorted using acoustophoresis or by dielectrophoresis prior to injecting the plurality of single cell droplets.

In one example, preferably, acoustophoresis, in particular, surface acoustic waves are utilized to move selected droplets into different sorting bins, as described for example in US 20130213488 A1.

In a further preferred embodiment, single cell droplets are sorted prior to injecting using the methods described in, for example, WO2016059182.

As known to the skilled in the art, some of these methods (such as magnetophoresis, acoustophoresis or electrokinetic mechanisms) might require labeling of the single cells. However, the type of label and if a label is required might depend on the cells to be analyzed. To give an example, for magnetophoresis, for example, cells might be labeled with a magnetic particle, however, erythrocytes, for example, may be sorted based on their natural iron content. Alternatively, in some examples, some types of cells might be manipulated using ferrofluids or paramagnetic solutions.

In most embodiments, the single cell droplets further comprise a fluorescent dye.

A "fluorescent dye" herein refers to a fluorescent substance that can re-emit light upon light excitation.

In some embodiments, when used, for example, in context of cell sorting, the fluorescent dye is conjugated to an antibody that recognizes a target feature on or in the cell; the dye may also be attached to a chemical entity with affinity for the cell membrane or another cellular structure. In some embodiments, the fluorescent dye recognizes a cellular structure.

In some embodiments, a fluorescent dye includes, but is not limited to reactive and conjugated dyes, nucleic acid dyes, cell function dyes, and fluorescent proteins or fluorescent nanoparticles.

"Reactive and conjugated dyes" include, but are not limited to xanthene (such as fluorescein), rhodamine, coumarine and cyanine dyes or derivatives thereof such as the Alexa fluor dyes.

"Nucleic dyes" include, but are not limited to, Sytox dyes, DRAQ7, propidium iodide (PI), and 7-aminoactinomycin D (7-AAD).

"Amine dyes" bind to the amine groups of cellular proteins. Those dyes bind to proteins of the cellular surface or to intracellular proteins of dead cells.

"Cell function dyes" are dyes that become fluorescent in specific metabolic conditions of a cell and include, for example, calcein. Calcein becomes fluorescent when binding intracellular $Ca^{2+}$.

"Fluorescent proteins" are known to the skilled in the art and include but are not limited to GFP or EBFP.

"Fluorescent nanoparticles" include but are not limited to, for example, PAN particles.

As it will be understood by the skilled in the art, some of the sorting techniques mentioned above, might require the introduction of a particle into the single cell droplet.

Accordingly, in some embodiments, the single cell droplets might further comprise at least one particle of a second type.

In some embodiments, the at least one particle of a second type herein refers to at least 1, at least 2 at least 3, such as more than one, such as 1 to 10, 1 to 5, 1 to 3 particles.

In some embodiments, the particle of a second type is fluorescent.

In some embodiments, said particle of a second type is selected from the group consisting of elastomeric particle, hydrogel particle, a polymeric particle or a magnetic particle, preferably a hydrogel particle or a magnetic particle, wherein the magnetic particle and the hydrogel particle are as defined herein below in the section "oligonucleotides".

In some embodiments the magnetic particle is a paramagnetic particle or a super paramagnetic particle.

"Elastomeric particles" herein refer for example to silicone elastomeric particles.

In some embodiments, the particle of a second type is functionalized so that they could have other molecules attached, such as proteins, nucleic acids or small molecules. Methods to functionalize a particle are known to the skilled in the art.

In some embodiments, the particle of a second type is functionalized with antibodies. The particle of a second type may be functionalized with an antibody using a, for example, a streptavidin-biotin link, as described herein below in the section RT-droplets in context with the particles of a first type.

In some embodiment, said antibody is directed against a component of the single cell.

The "cell" in context of the present invention is given its ordinary meaning as used in biology, for example a cell refers to an autonomous self-replicating unit that may exist as functional independent unit of life, for example for unicellular organism, or as sub-unit in a multicellular organism, for example in plants and mammals, that is specialized into carrying out particular functions towards the cause of the organism as a whole. However, a "cell" may further refer to quiescent cells which typically are still capable of cell division when mitotic stimulation is applied.

In some embodiments, cells refer to prokaryotic cells or eukaryotic cells, preferably, eukaryotic cells.

The defining feature distinguishing an "eukaryotic cell" from a prokaryotic cell is that they have membrane-bound organelles, especially the nucleus, which contains the genetic material, and is enclosed by the nuclear envelope.

An "eukaryotic cell" in context of the present invention is selected from the group consisting of a mammal cells, plant cell and fungal cell, preferably mammalian cell.

A "mammal" herein refers to any mammal, including humans, domestic and farm animals, and zoo, sports, or pet animals, such as dogs, cats, cattle, horses, sheep, pigs, goats, rabbits, etc. Preferably, the mammal is human.

Accordingly, in some embodiments, the cell is a mammalian cell, an engineered mammalian cell or a cell line or a mammalian immune cell.

In some embodiments, the mammalian cell is an immune cell.

In some embodiments, an immune cell may be, but is not limited to, B cells, T cells, or hybridomas, preferably B cell.

In some embodiments, a cell or plurality of cells herein refers to different types of cells or to cells of the same type or origin exposed to different conditions.

In one particular embodiment, the cell is a non-mammalian cell.

In one further particular embodiment, the non-mammalian cell is a yeast cell, an avian cell or a shark cell.

As mentioned above, the single cell droplets usually comprise an aqueous composition, wherein said aqueous composition is typically adapted to the cells used and typically comprises a buffered solution as defined herein below.

As known to the skilled in the art cells contain nucleic acids, wherein nucleic acids are as defined herein above.

The cells in context of the processes of the invention are preferably living cells. Methods to separate living from dead cells are known to the skilled in the art.

Cell Lysis

As known to the skilled ion the art, the nucleic acid present in a single cell are released when said cells are lysed.

"Cell lysis" used in context of the present invention may be accomplished by enzymatic, physical, and/or chemical means, or any combination thereof, in particular enzymatic, physical, and/or chemical means. Other cell disruption methods may also be used. The cell lysis methods described herein below apply to the lysis of the cell when present in a droplet, such as the single cell droplet or fused droplet, or when present in the reservoir without a droplet.

Accordingly, in some embodiments, the single cell or cell is lysed in the lysis step in context of the processes of the invention using enzymatic, physical, and/or chemical cell lysis.

"Enzymatic methods" to remove cell walls is well-established in the art. The enzymes are generally commercially available and, in most cases, were originally isolated from biological sources. Enzymes commonly used include lysozyme, lysostaphin, zymolase, mutanolysin, glycanases, proteases, and mannose.

As known by the skilled in the art "chemical cell lysis" is achieved using chemicals such as detergents, which disrupt the lipid barrier surrounding cells by disrupting lipid-lipid, lipid-protein and protein-protein interactions. The ideal detergent for cell lysis depends on cell type and source. Nonionic and zwitterionic detergents are milder detergents. The Triton X series of nonionic detergents and 3-[(3-Cholamidopropyl)dimethylammonio]-I-propanesulfonate (CHAPS), a zwitterionic detergent, are commonly used for these purposes. In contrast, ionic detergents are strong solubilizing agents and tend to denature proteins, thereby destroying protein activity and function. SDS, an ionic detergent that binds to and denatures proteins, is used extensively in the art to disrupt cells.

"Physical cell lysis" refers to the use of sonication, heat shock, ice shock or electroporation.

In one example, the cells are lysed using cold shock. This might be achieved in context of the processes of the invention by cooling down, for example, the chip comprising single cells in the plurality of reservoirs.

As mentioned herein below, in some embodiments, the RT droplet or plurality of RT droplets, fused droplet or plurality of fused droplets, or the plurality of reservoirs comprise a lysis composition.

In some embodiments, the lysis composition comprises enzymes selected from the group consisting of lysozyme, lysostaphin, zymolase, mutanolysin, glycanases, proteases, and mannose.

In one preferred embodiment, the lysing composition in context of the present invention comprises magnesium chloride, a detergent, a buffered solution and an RNase inhibitor.

In some embodiments, the detergent is selected from the group consisting of Triton-X-100, NP-40, Nonidet P40, and Tween-20 and IGEPAL CA 630.

Nonlimiting examples of the buffered solution may include Tris-HCl, Hepes-KOH, Pipes-NaOH, maleic acid, phosphoric acid, citric acid, malic acid, formic acid, lactic acid, succinic acid, acetic acid, pivalic (trimethylacetic) acid, pyridine, piperazine, picolinic acid, L-histidine, MES, Bis-tris, bis-tris propane, ADA, ACES, MOPSO, PIPES, imidazole, MOPS, BES, TES, HEPES, DIPSO, TAPSO, TEA (triethanolamine), N-Ethylmorpholine, POPSO, EPPS, HEPPS, HEPPSO, Tris, tricine, Glycylglycine, bicine, TAPS, morpholine, N-Methyldiethanolamine, AMPD (2-amino-2-methyl-1,3-propanediol), Diethanolamine, AMPSO, boric acid, CHES, glycine, CAPSO, ethanolamine, AMP (2-amino-2-methyl-1-propanol), piperazine, CAPS, 1, 3-Diaminopropane, CABS, or piperidine (see also, www.reachdevices.com/Protein/BiologicalBuffers.html). Nonlimiting examples of RNase inhibitors may include RNase OUT, IN, SuperIN Rnase, and those inhibitors targeting a wide range of RNAse (e.g., A, B, C, 1 and T1).

As mentioned herein below in the section "Microfluidic process for barcoding single cell nucleic acids", the chemical lysis, when applied to droplets, occurs, typically after fusing the single cell droplet with the RT droplet. In some embodiments, the cell lysis occurs preferably after performing a phenotypic assay, as for example after step b) of the process for genotyping single cells having a phenotype of interest.

As it will be understood by the skilled in the art, the components such as the reverse transcriptase and reverse transcriptase composition and the lysis composition will be diluted when further components are added, for example, the lysis composition will be diluted when, in one example, the RT and single cell droplets are fused.

Accordingly, the concentrations given for the ingredients of the lysis composition are preferably given as final concentrations, for example after droplet fusion. The skilled in the art will thus understand to adapt the initial concentrations present in the reservoir, or the RT droplets.

In some embodiments, the concentration of magnesium chloride is 1 mM to 20 mM.

In some embodiments, the concentration of the detergent is 0.1% to 10%.

In one example, the lysis composition is typically 0.2% Triton, 3 mM $MgCl_2$, 50 mM Tris-HCl pH 7.4.

Reverse Transcription (RT)

In one step in context of the processes of the invention a plurality of RT droplets is injected, wherein at least some of the RT droplets comprise a reverse transcriptase (RT) and at least one oligonucleotide.

In context of the microfluidic process for genotyping single cells having a phenotype of interest the reverse transcriptase (RT) and at least one oligonucleotide is provided in each reservoir of the plurality of reservoirs.

A "reverse transcriptase (RT)" is an enzyme used to generate complementary DNA (cDNA) from a nucleic acid template, in particular a RNA template, in a process termed reverse transcription.

In some embodiments, the reverse transcriptase is selected from the group consisting of Superscriptase I, Superscriptase II, Superscriptase III, Superscriptase IV, Murine Leukemia RT, SmartScribe RT or MultiScribe RT.

In some embodiments, the reverse transcriptase has a template switch activity.

The template switch activity permits to uniquely label cDNA with a universal sequence. Using the template switch activity leads to uniquely labelling cDNA at its 5'end with said universal sequence. A universal sequence herein refers to sequences typically used for 5' Rapid Amplification of cDNA End (RACE). It is generally known to the skilled in the art how to perform 5'RACE and which universal sequence may be used.

In context of the processes of the present invention, reverse transcription takes place either after fusing the at least one droplet of the first type with at least one droplet of the second type or, optionally, when the process is performed without droplets, after step c) of the process of genotyping single cells having a phenotype of interest.

Accordingly, as described herein above in context of the lysis composition, it will be understood by the skilled in the art, that ingredients, such as the reverse transcriptase will be diluted when the different ingredients such as a lysis composition, the reverse transcriptase or the reverse transcription composition are mixed. Accordingly, the concentrations given for any ingredients herein below are preferably given as final concentrations, present, for example, after droplet fusion.

In some embodiments, the concentration of the reverse transcriptase is 1 to 50 U/µl, preferably 5 to 25 U/µl, for example at 12.5 U/µl.

"Reverse Transcription" or "RT reaction" is a process in which single-stranded RNA is reverse transcribed into a single-stranded complementary DNA (cDNA) by using total cellular RNA or poly(A) RNA, a reverse transcriptase enzyme, a primer, dNTPs and an RNase inhibitor. It will be understood by the skilled in the art, that the product of the reverse transcription is a RNA/DNA duplex comprising a single strand cDNA hybridized to its template RNA. As it will be further understood, said RNA/DNA duplex is further linked to the at least one oligonucleotide comprising the primer sequence used for the reverse transcription.

Accordingly, it will be understood by the skilled in the art that reverse transcribing the nucleic acids, for example in step b) of the microfluidic process for barcoding single cell nucleic acids, results in single cell cDNA.

Accordingly, in some embodiments, the at least some of the fused droplets further comprise single cell cDNAs produced by reverse transcription of nucleic acids from the single cell lysate.

Accordingly, in some embodiments, when no droplets are used, the reservoir further comprises single cell cDNAs produced by reverse transcription of nucleic acids from the single cell lysate.

In some embodiments, said cDNA refers to a single-stranded complementary DNA.

In a further embodiment, said cDNA is comprised in a RNA/DNA duplex.

In some embodiments, the RNA/DNA duplex refers to the RNA that has been reverse transcribed and is still hybridized either partially or over the entire length to the synthesized cDNA and/or the primer sequence of the at least one oligonucleotide.

As it will be understood by the skilled in the art, in some embodiments, the RNA/DNA duplex is linked to the at least one oligonucleotide comprising the primer sequence to which the nucleic acid, preferably mRNA was hybridized in the hybridization step, for example in step a), and which was used for reverse transcription in the reverse transcription step, for example in step b).

As it will be understood by the skilled in the art, in some embodiments the at least one oligonucleotide and thus the RNA/DNA duplex is linked to a particle of a first type.

In some embodiments, the plurality of reservoirs, the RT droplet or plurality of RT droplets or the fused droplet or plurality of fused droplets comprise a reverse transcriptase composition.

In some embodiments, a reverse transcriptase composition comprises a protease inhibitor, dNTPs and/or DTT, preferably protease inhibitor, dNTPs and DTT.

In some embodiments, the protease inhibitor comprises a plurality of protease inhibitors.

In some embodiments, the protease inhibitor is selected from the list consisting of Leupeptin hemisulfate salt, pepstatin A, AEBSF, Aprotinin, Bestatin hydrochloride, E-64 and PMSF.

For example, the protease inhibitor may comprise one or more of Leupeptin hemisulfate salt, pepstatin A, AEBSF, Aprotinin, Bestatin hydrochloride, E-64 and PMSF.

As used herein, the term "dNTP" refers to a deoxynucleoside triphosphate, e.g. deoxyadenosine-5'-triphosphate (dATP, "A"), deoxycytidine-5'-triphosphate (dCTP, "C"), deoxyguanosine- 5'-triphosphate (dGTP, "G"), deoxythymidine-5'-triphosphate (dTTP, "T") or deoxyuridine-5'-triphosphate (dUTP, "U"). The term "dNTP" is intended to refer also to deoxynucleoside triphosphates comprising modified bases and base analogues that are capable of mimicking the base pairing of A, C, G, T, or U, or that are capable of base pairing in a degenerate mode, e.g., a base that pairs with A or G, C or T, A or C, G or T, G or C, or A or T, called nucleotide analogues. Said nucleotide analogues may be used, for example, for purification, as further explained herein below.

The skilled in the art will understand that the concentrations given for the ingredients of the reverse transcriptase composition are preferably given as final concentrations, present, for example, in the fused droplet after droplet fusion.

In some embodiments, the concentration of DTT is 1 mM to 10 mM, preferably 5 mM.

In some embodiments, the concentration of dNTP is 0.01 mM to 10 mM, preferably 0.1 to 1 mM, more preferably 0.5 mM.

In some embodiments, a reverse transcriptase composition further comprises a RNase inhibitor. The RNase inhibitor is defined herein above in the section "Cell lysis".

Oligonucleotide

The term "oligonucleotide" is as defined herein above.

The "at least one oligonucleotide" in context of the microfluidic processes of the invention comprises a primer sequence.

A "primer sequence" is typically a short single-stranded nucleic acid, of between 10 to 50 nucleotides in length, designed to perfectly or almost perfectly match a nucleic acid of interest, to be captured and then amplified by typically PCR or reverse transcribed by typically RT. The primer sequences are "specific" to the nucleic acids they hybridize to, i.e. they preferably hybridize under stringency hybridization conditions, more preferably under high stringency hybridization conditions, or are complementary to or almost complementary to the nucleic acids they hybridize to, also called target sequence.

"Stringent condition" or "high stringency condition" are as defined herein above.

Typically, the primer sequence serves as a starting point for nucleic acid synthesis, allowing polymerase enzymes such as nucleic acid polymerase to extend the primer sequence and replicate the complementary strand. A primer sequence may be complementary to and hybridize to a target nucleic acid. In some embodiments, a primer sequence is a synthetic primer sequence.

In some embodiments, a primer sequence is a non-naturally-occurring primer sequence. A primer sequence typically has a length of 10 to 50 nucleotides. For example, a primer sequence may have a length of 10 to 40, 10 to 30, 10 to 20, 25 to 50, 15 to 40, 15 to 30, 20 to 50, 20 to 40, or 20 to 30 nucleotides. In some embodiments, a primer sequence has a length of 18 to 24 nucleotides.

In some embodiments, the primer sequence is selected from the group consisting of a poly-T sequence, a random DNA sequence, and a gene-specific sequence.

A "poly T sequence" as herein referred to is a sequence comprising 10 to 50, 10 to 40, 10 to 30, 10 to 20, 25 to 50, 15 to 40, 15 to 30, 20 to 50, 20 to 40, or 20 to 30 thymine "T". The Poly T sequence hybridizes with the poly A tail present in mRNAs.

In some embodiments, the random DNA sequence can be of any suitable length, such as 6 to 50, 6 to 50, 6 to 40, 6 to 30, 6 to 20, 10 to 50, 10 to 40, 25 to 50, 15 to 40, 15 to 30, 20 to 50, 20 to 40, or 20 to 30 nucleotides.

In one particular embodiment, the primer sequence is a gene-specific sequence and the gene is selected from the group consisting of antibody heavy chain variable gene, antibody heavy chain constant gene, antibody light chain variable gene, antibody light chain constant gene, alpha T-cell receptor gene (either variable or constant), beta T-cell receptor gene (either variable or constant), delta T-cell receptor gene (either variable or constant) or genes selected for a panel for transcriptome analysis.

The term "antibody" in the wording "antibody heavy chain variable gene", "antibody heavy chain constant gene", "antibody light chain variable gene" and "antibody light chain constant gene" is as defined herein above.

The term "T-cell receptor" in the wording "alpha T-cell receptor gene", "beta T-cell receptor gene" and "delta T-cell receptor gene" or "gamma T-cell receptor gene" is as defined herein above.

The word "gene" is as defined herein above.

The skilled in the art will understand that the number of the at least one oligonucleotide present in each reservoir of the plurality of reservoirs or present in one RT droplet will be adapted to the number of different nucleic acids, in particular to the number of RNAs, that are to be transcribed and barcoded from one single cell.

Accordingly, "at least one" in the wording "at least one oligonucleotide" refers to the number of different oligonucleotides present in one droplet or reservoir, wherein one oligonucleotide of the at least one oligonucleotide differs from another oligonucleotide by its primer sequence.

In some embodiments, "at least one" in the wording "at least one oligonucleotide" refers to at least 2, at least 3, at least 4, at least 5, at least 6, at least 7, at least 8, at least 9 at least 10 oligonucleotides. In some embodiments, at least one oligonucleotide refers to 1 to 100 oligonucleotides, 1 to 80, 1 to 60, 1 to 40, 1 to 30, 1 to 20, 1 to 10, preferably, 1, 2, 3, 4, 5, 6, 7, 8, 9 oligonucleotides.

It will be understood that "at least one oligonucleotide" thus refers to at least one oligonucleotide which is present in the RT droplet or in each reservoir at a certain concentration and, accordingly, one oligonucleotide from the at least one oligonucleotide thus refers to a plurality of oligonucleotides of the same sequence.

It will be further understood by the skilled in the art that when, for example, the transcriptome of a cell is to be transcribed and barcoded, oligonucleotides having a primer sequence specific to all mRNAs will be used, such as poly T primer sequences, as further defined herein below, whereas, when a gene specific transcriptome is to be transcribed and barcoded, oligonucleotides comprising a gene specific primer sequence are used, as further defined herein below.

It will be thus understood, that the number of oligonucleotides corresponds to at least the number of specific genes of which the transcriptome is to be transcribed and barcoded.

In one specific embodiment, the at least one oligonucleotide is at least two oligonucleotides, wherein one of the at least two oligonucleotides comprises a primer sequence specific to one gene, such as an antibody heavy chain variable gene and wherein the other oligonucleotide comprises a primer sequence specific for another gene, such as an antibody light chain variable gene.

In another particular embodiment, the at least one oligonucleotide is at least two oligonucleotides, wherein one of the at least two oligonucleotides comprises a primer sequence specific for, for example, the alpha T-cell receptor gene or the beta T-cell receptor gene or gamma T-cell receptor, and wherein the other of the at least two oligonucleotides comprises a primer sequence specific for, for example, the delta T-cell receptor gene.

In another particular embodiment, the at least one oligonucleotide is at least three oligonucleotides, wherein the first of the at least three oligonucleotides comprises a primer sequence specific for, for example, the alpha T-cell receptor gene and the second of the at least three oligonucleotides comprises a primer sequence specific for, for example, the beta T-cell receptor gene, and wherein the third of the at least three oligonucleotides comprises a primer sequence specific for, for example, the polyA mRNA.

The "transcriptome" generally refers to the set of all messenger RNA molecules in one cell or a population of cells. Accordingly, the "transcriptome of a cell" or "the transcriptome of a single cell" herein refers to the set of all messenger RNA molecules in one cell.

As it will be understood by the skilled in the art, a gene specific transcriptome thus refers to the set of all messenger RNA molecules derived from one gene.

As it is known by the skilled in the art, different gene products, so called isoforms, may be encoded by one gene. Accordingly, a gene specific transcriptome may further refer to the messenger RNA molecules of at least one specific isoform of one specific gene, such as the messenger RNA molecules of 1, 2, 3, 4 or more specific isoforms of one specific gene or to the messenger RNA molecules of all isoforms of one specific gene.

Accordingly, in some embodiments, the single cell nucleic acid in context of the present invention is RNA, wherein RNA is as defined herein above.

In a further embodiment, mRNA comprises a poly A sequence, also called poly A tail.

Furthermore, in some particular embodiments, the "at least some of the nucleic acids" in context of the present invention refers to at least one nucleic acid, preferably, at least 2, at least 3, at least 4, at least 5, nucleic acids or more. In one particular, the nucleic acids of step a) and b) refer to 1, 2, 3, 4, 5, 6, 7, 8, 9 or 10 nucleic acids.

The processes of the invention can be used to reverse transcribe from one specific nucleic acid up to all nucleic acids of a single cell.

Accordingly, in further embodiments, the "at least some of the nucleic acids" in context of the present invention refers to from 1 to 100000 nucleic acids, such as 1 to 80000, 1 to 60000, 1 to 40000, such as 1, 1000, 2000, 4000, 6000, 8000, 10000, 12000, 14000, 16000, 20000, 25000, 30000, 45000, 50000 nucleic acids. Accordingly, in some embodiments, the nucleic acid herein refers to the RNA of all genes.

As mentioned above, the processes of the invention also refer retrotranscribing a gene specific transcriptome.

Accordingly, in some embodiments, the nucleic acid herein refers to the RNA of at least one specific gene.

Said at least one specific gene may be at least one, at least 2, at least three, at least four at least five, such as 1 to 10, 1 to 5 genes, for example 1, 2, 3, 4, 5, 6, 7, 8, 9, or 10 genes.

In some embodiments, said at least one specific gene is selected from the group consisting of antibody heavy chain variable gene, antibody heavy chain constant gene, antibody light chain variable gene, antibody light chain constant gene, alpha T-cell receptor gene, beta T-cell receptor gene, and delta T-cell receptor gene and gamma T-cell receptor gene.

In some embodiments, specific genes can also be selected to further gain information of cell phenotype and to classify the cells based on gene expression.

In some embodiments, the at least one oligonucleotide further comprises a promoter and/or a spacer sequence.

The promoter and/or the spacer sequence are preferably located towards the 5' end or located at the 5' end of the primer sequence. Examples of promoter sequences include, but are not limited to, T7 promoters, T3 promoters, or SP6 promoters.

In some embodiments, the oligonucleotide further comprises a barcode sequence.

Accordingly, in some embodiments the oligonucleotide comprises from 5' to 3' a barcode sequence and a primer sequence.

The "barcode sequence" or simply called "barcode" herein refers to a unique nucleic acid sequence that can be distinguished by its sequence from another nucleic acid sequence, thus permitting to uniquely label a nucleic acid sequence so that it can be distinguished from another nucleic acid carrying another barcode sequence.

In some embodiments, the barcode sequence uniquely identifies the nucleic acids released by a single cell from nucleic acids released from other cells, for instance, even after the nucleic acids are pooled together.

In some embodiments, the barcode sequence is used to distinguish tens, hundreds, or even thousands of nucleic acids, e.g., arising from different cells or other sources.

In some embodiments, the barcode sequence is of any suitable length. The barcode sequence is preferably of a length sufficient to distinguish the barcode sequence from other barcode sequences. In some embodiments, a barcode sequence has a length of 1 to 5, 1 to 10, 5 to 15, or more than 15 nucleotides such as 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 72, 74, 76, 78, 80, 85, 90 or more nucleotides, such as 50 to 85, 60 to 80, 70 to 80 nucleotides.

In some embodiments, the barcode sequence consists of more than one barcode sequence and thus may be referred to as "at least one barcode sequence".

In a related embodiment, the different barcode sequences may be taken from a "pool" of potential barcode sequences, which themselves have typically been generated by split and poll synthesis. If the barcode sequence consists of more than one barcode sequence, the barcode sequences may be taken from the same, or different pools of potential barcode sequences. The pool of sequences may be selected using any suitable technique, e.g., randomly, or such that the sequences allow for error detection and/or correction, for example, by being separated by a certain distance (e.g., Hamming distance) such that errors in reading of the barcode sequence can be detected, and in some cases, corrected. The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences.

Methods to join different barcode sequences taken from one "pool" or more than one pool are known to the skilled in the art and include, but are not limited to, the use of ligases and/or using annealing or a primer extension method.

Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, Taq DNA Ligase, or the like. Many such ligases may be purchased commercially.

In some embodiments, the barcode sequence is a double stranded or single stranded nucleic acid.

In some embodiments the oligonucleotide further comprises a unique molecular identifier (UMI). The UMI is located at the 3' end or the 5' end of the barcode sequence.

"Unique molecular identifier" (UMI) sequences are well known to the skilled in the art and are described, for example in Kivioja et al (Nature Method, 2012, vol 9, N° 1). The UMI sequences allow bioinformatic removal of duplicated reads.

In some embodiments, the at least one oligonucleotide is introduced into the reservoir or the droplets, in particular into the RT droplets, by initially binding the at least one oligonucleotide to at least one particle of a first type.

It will be understood by the skilled in the art that binding the at least one oligonucleotides temporally to a particle permits to provide particles having a high amount of oligonucleotides. Furthermore, binding the at least one oligonucleotide initially to the particle facilitates, in particular when droplets are used, the introduction of the at least one oligonucleotides into each droplet, such as the RT droplet.

Accordingly, in some embodiments the reservoir or the RT-droplet further comprises at least one particle of a first type to which the at least one oligonucleotide is bound.

At least one particle of a first type herein refers to at least one, two, three, four, five or more particles of a first type, preferably one particle of a first type.

As it will be understood by the skilled in the art and as explained herein above, the number of the particles of a first type encapsulated in one RT droplet and the size of the droplets follow a probability distribution, for example a Poisson distribution, and depends on the concentration of the particles of a first type, the injection parameters of the aqueous composition, such as the reverse transcription composition or lysis composition, the geometry of the main channel, the injection parameters of the particles of the first type and the carrier fluid.

Accordingly, in some embodiments, the parameters can be adapted to obtain RT droplets with 2, 1 or 0 particles of a first type in it, thus avoiding droplets containing more than 2 particles of a first type.

In a related embodiment, the parameters can be adapted to obtain RT droplets with 1 or 0 particles of a first type in it, thus avoiding droplets containing more than 1 particle of a first type.

In some embodiments, the at least one particle of a first type is encapsulated within the RT droplets at no more than about 2 particles of a first type/droplet, preferably, in a further embodiment, the at least one particle of a first type is encapsulated are encapsulated within the droplets at no more than about 1 particle/droplet, or the at least one particle of a first type is encapsulated within the droplets preferentially with 1 particle/droplet, or the at least one particle of a first type is encapsulated within the droplets with an average of 1 particle/droplet.

In analogy, when no droplets are used, in some embodiments, each reservoir preferably comprises no more than about 2 particles of a first type/reservoir, preferably, no more than about 1 particle/reservoir, or 1 particle/reservoir, or an average of 1 particle/reservoir.

The "particle", such as the particle of a first type or particle of a second type, in context of the present invention refers to a microparticle.

In some embodiments, the particle is a hydrogel particle, a polymeric particle or a magnetic particle.

The particle may have irregular or regular shape. For example, the particle can be spherical, ellipsoidal, or cubic.

In some embodiments, the particle in context of the present invention is a hydrogel particle.

"Hydrogel particles" are for example described in the International Patent Application No. WO 2008/109176, entitled "Assay and other reactions involving droplets". Examples of hydrogels include, but are not limited to agarose, poly(ethylene glycol) diacrylate, or acrylamide-based gels, such as bis-acrylamide, polyacrylamide, streptavidine acrylamide, poly-N-isopropylacrylamide, or poly N-isopropylpolyacrylamide or mixtures thereof. In one example the hydrogel particle comprises acrylamide, bis-acrylamide and strepatvidine acrylamide.

In another set of embodiments, the particles comprise one or more polymers and are thus herein referred to as "polymeric particle". Exemplary polymers include, but are not limited to, polystyrene (PS), polycaprolactone (PCL), polyisoprene (PIP), poly(lactic acid), polyethylene, polypropylene, polyacrylonitrile, polyimide, polyamide, and/or mixtures and/or co-polymers of these and/or other polymers.

In addition, in some embodiments, the particle is magnetic and is thus referred to as "magnetic particle", which could allow for the magnetic manipulation of the particles.

For example, the magnetic particles may comprise iron or other magnetic materials.

The particles, in particular the particles of a first type or of a second type, could also be functionalized so that they could have other molecules attached, such as proteins, nucleic acids or small molecules. Thus, some embodiments of the present invention are directed to a set of particles defining a library of, for example, nucleic acids, proteins, small molecules, or other species such as those described herein. In one example, said particle is functionalized with an antibody. In some embodiments said antibody is directed against a component of a cell.

In some embodiments, the particle, in particular the particle of a first type, is fluorescent.

In some embodiments, the particle comprises streptavidin. Streptavidin may be coupled to the surface of the particle defined herein above.

In some embodiments the particles of a first or a second type have a size from 0.1 pL to 100 pL, such as 0.1 pL to 500 pL, 0.1 pL to 400 pL, 0.1 pL to 400 pL, 0.1 pL to 300 pL, for example 0.5 pL to 300 pL, 0.5 pL to 250 pL, 0.5 pL to 200 pL, 1 pL to 250 pL, 1 pL to 200 pL, preferably 1 pL to 200 pL, typically 100 pL to 200 pL, such as 150 pL.

In some embodiments, the at least one oligonucleotide is covalently linked or non-covalently linked to at least one particle of a first type, wherein the at least one particle of a first type is defined herein above.

"Non-covalently linked" herein refers, for example, to a streptavidin-biotin bond. Other non-covalent bonds are known to the skilled in the art, such as avidin biotin bonds or his tag and nickel bonds.

"Covalently linked" herein refers for example to an amino bond or an acrylic phosphoramidite bond.

"Streptavidin" generally refers to a 52.8 kDa protein purified from the bacterium *Streptomyces avidinii*. Streptavidin homo-tetramers have an extraordinarily high affinity for biotin with a dissociation constant (Kd) on the order of $\approx 40^{-14}$ mol/L, the binding of biotin to streptavidin is one of the strongest non-covalent interactions known in nature.

In a preferred embodiment, the non-covalent bond is a streptavidin-biotin link.

Streptavidin-Biotin bonds are known to the skilled in the art.

Accordingly, in some embodiments, the particle of a first type, for example, comprises streptavidin and in the same embodiment, the at least one oligonucleotide, comprises biotin. In other words, the at least one type of oligonucleotide is functionalized with biotin.

Independent of the type of bond used to link the at least one type of oligonucleotide to the particle of a first type, the at least one type of oligonucleotide may further comprise at least one linker sequence.

Accordingly, in a further embodiment, the "at least one type of an oligonucleotide" or simply the "oligonucleotide" further comprises at least one linker sequence, said linker sequence is preferably comprised close to the 5' end.

In some cases, the oligonucleotide may contain further to the primer sequence mentioned above at one or more primer sequences for sequencing. Examples of such primer sequences for sequencing include, but are not limited to, P5 primer, P7 primer, PE1 primer, PE2 primer, A19 primer, or other primers discussed herein.

Accordingly, in some embodiments, the at least one type of an oligonucleotide comprises from 5' to 3' optionally a linker sequence, optionally a promoter sequence, optionally a primer sequence for sequencing, optionally a barcode sequence, optionally a UMI and a primer sequence.

It will be thus understood by the skilled in the art that, in some embodiments, the at least one oligonucleotide is bound to the particle of a first type via the 5' end.

However, in some alternative embodiments the at least one oligonucleotide may be bound to the particle of a first type via the 3' end.

In some embodiments, the "linker sequence" is a sequence with which the at least one oligonucleotide is optionally linked to the particle of a first type.

"Optionally linked herein" refers to the possibility that once the at least one type of oligonucleotide linked to the particle is loaded into the RT droplets or the plurality of RT droplets or the reservoirs, the at least one type of oligonucleotide might be released, so that the RT droplet or the fused droplet or the reservoir comprises the particle of a first type and the at least one oligonucleotide without the at least one type of oligonucleotide being linked to said particle of a first type.

Preferably, the linker sequence is a cleavable linker sequence, e.g., that can be cleaved upon application of a suitable stimulus, such as enzymatic and/or photocleavage.

"Cleavable linkers" may include, but are not limited to, TEV, trypsin, thrombin, cathepsin B, cathespin D, cathepsin K, caspase lumatrix metalloproteinase sequences, phosphodiester, phospholipid, ester, -galactose, dialkyl dialkoxysilane, cyanoethyl group, sulfone, ethylene glycolyl disuccinate, 2-N-acyl nitrobenzenesulfonamide, a-thiophenylester, unsaturated vinyl sulfide, sulfonamide after activation, malondialdehyde (MDA)-indole derivative, levulinoyl ester, hydrazone, acylhydrazone, alkyl thioester, disulfide bridges, azo compounds, 2-Nitrobenzyl derivatives, phenacyl ester, 8-quinolinyl benzenesulfonate, coumarin, phosphotriester, bis-arylhydrazone, bimane bi-thiopropionic acid derivative, paramethoxybenzyl derivative, tert-butylcarbamate analogue, dialkyl or diaryl dialkoxysilane, orthoester, acetal, aconityl, hydrazone, b¬thiopropionate, phosphoramidate, imine, trityl, vinyl ether, polyketal, alkyl 2-(diphenylphosphino)benzoate derivatives, allyl ester, 8-hydroxyquinoline ester, picolinate ester, vicinal diols, and selenium compounds (see, e.g. Leriche G, Chisholm L, Wagner A).

Cleavable linkers are well known to the skilled in the art and are further described in Chemical Biology, for example in Leriche H. et al. (Bioorg Med Chern. 15; 20(2):571-82. 2012). Cleavage conditions and reagents include, but are not limited to, enzymes, nucleophilic/basic reagents, reducing agents, photo-irradiation, electrophilic/acidic reagents, organometallic and metal reagents, and oxidizing reagents.

In some embodiments, the processes of the invention further comprise a step of releasing the at least one oligonucleotide bound to the at least one particle of a first type from said particle, for example, after it has been incorporated into the RT droplets or after it has been provided in the reservoir.

Furthermore, in some embodiments, the at least one oligonucleotide initially bound to the at least one particle of a first type is released from said at least one particle of a first type prior to reverse transcribing the single cell nucleic acids.

In some embodiments, the step of releasing the at least one oligonucleotides may occur prior or after fusing the single cell and the RT droplets, after lysing the cells and/or before reverse transcribing the single cell nucleic acids nucleic acids.

The skilled in the art will understand that depending on the time point selected for releasing the at least some of the oligonucleotides, the term "at least some of the oligonucleotides" might refer to, for example, at least some of the oligonucleotides hybridized to the nucleic acids released by the cells or to a DNA/RNA duplex, as defined herein above.

In some embodiments, the at least some of the oligonucleotides can be released using any means, such as enzymes, nucleophilic/basic reagents, reducing agents, photo-irradiation, electrophilic/acidic reagents, organometallic and metal reagents, and oxidizing reagents.

In some embodiments, the at least one oligonucleotide can be released using enzymatic and/or photo cleavage. For example, an endonuclease may be used to cleave a linker sequence or any other sequence to release the at least some of the oligonucleotides from the particle of a first type.

In a further embodiment, releasing the oligonucleotide refers to disrupting the bond, such as a streptavidin biotin bond. Methods to disrupt a streptavidin biotin bond are known to the skilled in the art and include enzymatic digestion of streptavidin and/or denaturation of streptavidin.

In some embodiments, the oligonucleotide is released by enzymatic digestion of streptavidin.

The concentration of the at least one oligonucleotide is at least 10 nM, preferably at least 100 nM.

In some embodiments, the concentration of the at least one oligonucleotide is at least 150 nM, at least 200 nM, at least 300 nM, at least 400 nM, at least 500 nM, at least 600 nM, at least 700 nM, at least 800 nM, at least 900 nM and at least 1 µM, such as for instance 100 nM to 5 µM, 100 nM to 4 µM, 100 nM to 3 µM, 100 nM to 2 µM, 100 nM to 1 µM, preferably 100 nM to 500 nM.

In one example, the primer sequence is a poly T primer sequence and the concentration of the at least one oligonucleotide is 100 nM to 3300 nM (corresponding to 3.3 µM).

In a further example, the primer sequence is a gene specific primer sequence and the concentration of the at least one oligonucleotide is 100 nM or 1000 nM (corresponding to 1 µM).

In some embodiments, the concentration of each oligonucleotide of the at least one oligonucleotide in the microfluidic droplets is at least 10 nM, preferably at least 100 nM.

In some embodiments, the concentration of each oligonucleotide of the at least one oligonucleotide is at least 150 nM, at least 200 nM, at least 300 nM, at least 400 nM, at least 500 nM, at least 600 nM, at least 700 nM, at least 800 nM, at least 900 nM and at least 1 µM, such as for instance 100 nM to 5 µM, 100 nM to 4 µM, 100 nM to 3 µM, 100 nM to 2 µM, 100 nM to 1 µM, preferably 100 nM to 500 nM.

According to the above, in some embodiments, the reservoir, the RT droplet or plurality of RT droplets further comprise a lysis composition, wherein said lysis composition is defined herein above in the section "cell lysis".

In some embodiments, the concentration of the at least one oligonucleotide refers to the concentration in the reservoir, in the RT droplet or in the fused droplet.

In some embodiments the RT droplets may be screened and sorted prior to injecting a plurality of RT droplets.

Accordingly, in some embodiments the RT droplets further comprise a particle of a second type, wherein said particle of a second type is as defined in the section "single cells".

Accordingly, in some further embodiments, the RT droplets further comprise a dye as defined herein above.

Amplifying and Sequencings

In some embodiments the processes of the invention further comprise the step of amplifying the barcoded single cell cDNA after recovering said barcoded single cell cDNA. In some embodiments, said amplification step is performed after removing unincorporated oligonucleotides. In some embodiments, said amplification step is performed prior to the sequencing step defined herein below.

In some embodiments, the amplifying step is performed in a multiplex reaction, a separated polymerase chain reaction (PCR) (see FIG. 11), isothermal amplification, or a linear amplification.

In some embodiments, the linear amplification is an in vitro transcription.

In some embodiments, the barcoded single cell cDNA produced in the processes of the invention is quantified using qPCR, such as simplex and/or multiplex qPCR reaction.

In a further embodiment the processes of the invention further comprise a step of sequencing the barcoded single cell cDNA.

In context of the present invention, in some embodiments, the step of sequencing the barcoded single cell cDNA herein refers to first contacting the barcoded single cell cDNA to a sequencing library and amplifying the sequences of interest from the sequencing library that correspond to the barcoded single cell cDNA, respectively.

Figure 12:
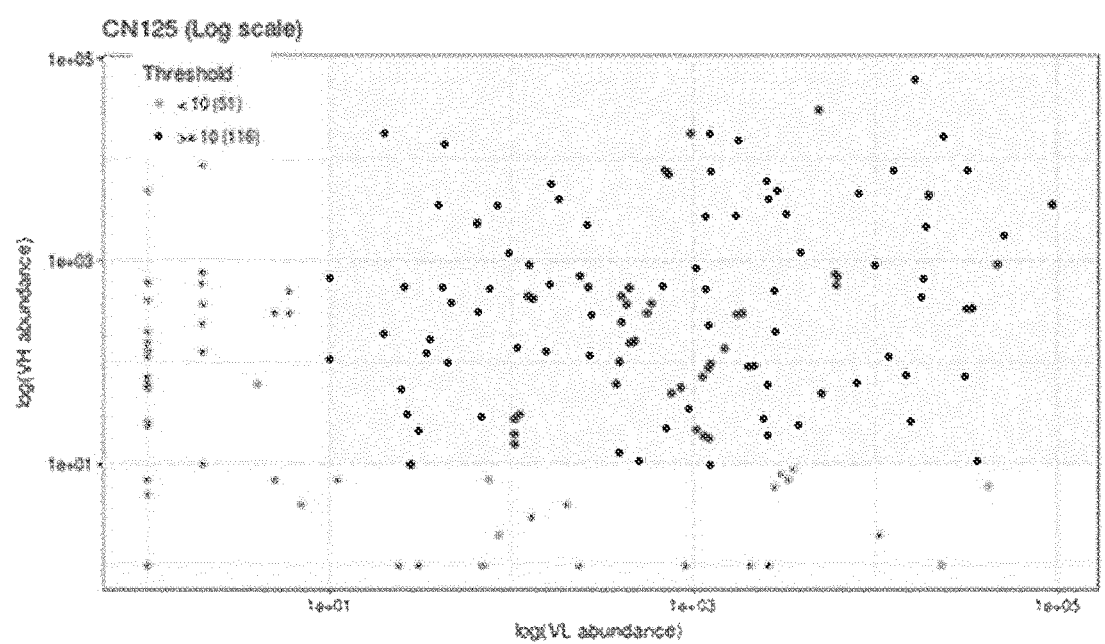
FIG. 12 shows several steps performed during the NGS sequence analysis. One of them consist in pairing the VH sequence of a single cell IgG producing cell with a VL. The graph shows the log (abundance of reads) used for pairing VH and VL.

In some embodiments, the step of sequencing the barcoded single cell cDNA may comprise performing a next generation sequencing (NGS) protocol on a sequencing library (see FIG. 12).

In certain embodiments, the NGS protocol comprises loading an amount of the sequencing library between 4 pM to 20 pM per flow cell of a reagent kit.

In some embodiments, the NGS sequencing protocol further comprises the step of adding 5-60% PhiX to the amount of the sequencing library or to the flow cell of the reagent kit.

Microfluidic Process for Barcoding Single Cell Nucleic Acids

"Barcoding" herein refers to adding a genetic sequence, a so-called barcode sequence as defined herein above in the section "oligonucleotide", to a nucleic acid which allows distinguishing said barcoded nucleic acid from a nucleic acid having another added genetic sequence, i.e. another unique barcode sequence.

Figure 8:
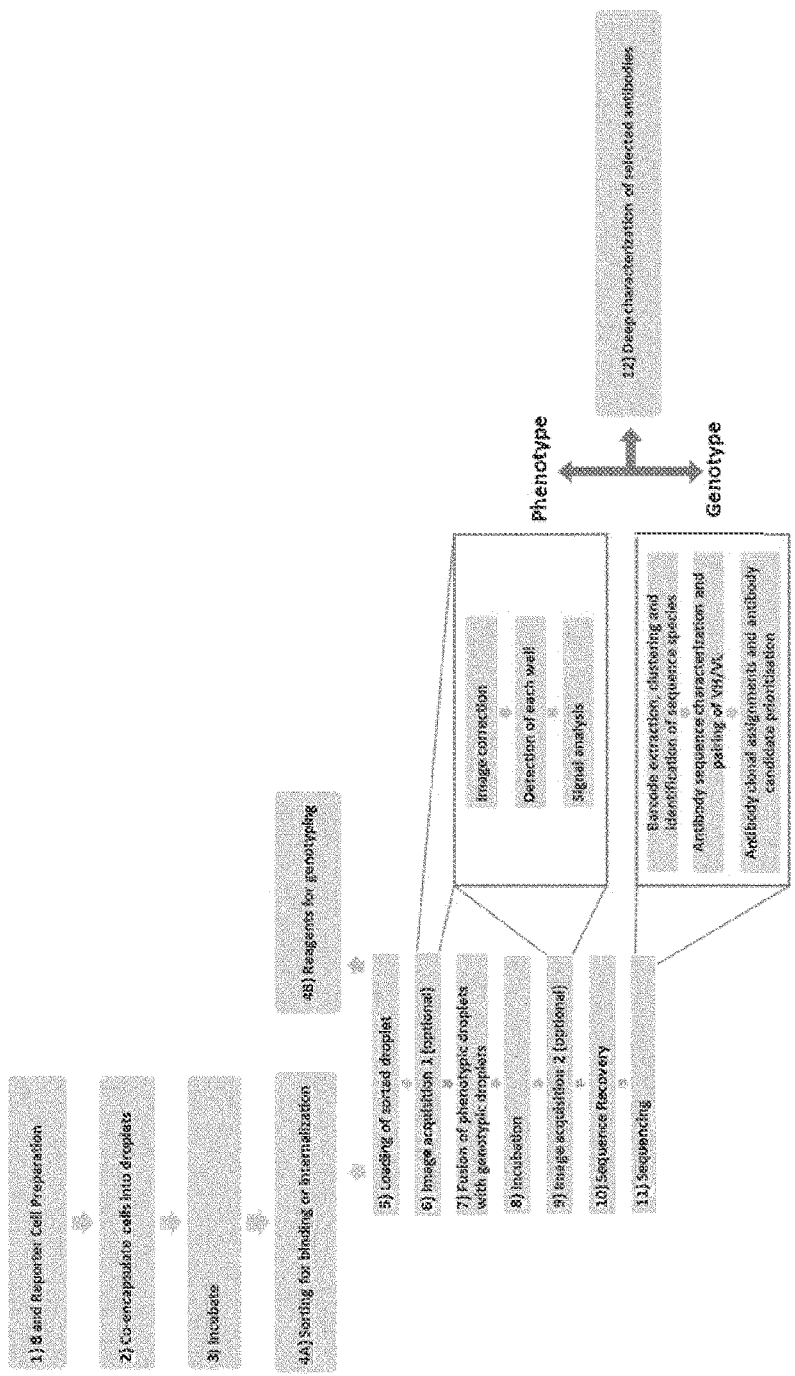
FIG. 8 shows an example of a standard procedure used for screening of IgG producing cells in droplet. Step 1, involve a b cells and reporter cells preparation. The b cells population is preliminary enriched to increase the relative amount of IgG secreting or producing cells among other type of irrelevant population. Step 2, elicit the co-encapsulation of a single b cell and one single or multi-reporter cell. Step 3, the emulsion containing cells is incubated to let the IgG producing cells secrete the antibody in the droplet. Step 4A, a sorting is applied to the population of interest evolving the isolation of IgG specific antibody inducing specific phenotype function (binding, . . . ). Step 4B, an emulsion containing reagents for performing a reverse transcription (RT) in droplet is prepared in parallel of the 4A step. Step 5, the sorted droplets are dispensed inside a microfluidic device, containing a plurality of reservoir. The sorted droplet will be trapped by buoyancy inside the microfluidic device. Step 6, the trapped droplet containing cells and presenting the phenotype of interest, are then imaged by using an epifluorescence-based microscope or any other device for fluorescence and/or luminescence acquisition. Step 7, in a subsequent step the emulsion produced at the step 4B is dispensed inside the microfluidic device and fused as one single sorted droplet is fused with one single RT droplet. Step 8, an incubation step is performed to allow the reverse transcription, eventually coupled to PCR reaction, to occur. Step 9, after incubation, the microfluidic device is imaged by using an epifluorescence-based microscope or any other device for fluorescence and/or luminescence acquisition. Step 10, emulsion trapped in the microfluidic device is recovered and eventually processed for library amplification by PCR. Step 11, the amplified libraries is sent for sequencing. After completing this entire process two steps of data analysis are performed. Related to the step 6 and 9, the images are analysed following three general steps, image correction, detection of each individual well/signal and the signal analysis giving the phenotype of the said droplet. Related to the step 11, the data of sequencing are analysed following three general steps, 1) barcode extraction, clustering and identification of sequences species, 2) Antibody sequence characterization and pairing of VH/VL, 3) Antibody clonal assignments and antibody candidate prioritisation. Step 12, the combination of these two analysis allows the deep characterization of the selected antibodies and the link between the phenotype and genotype.
Figure 9:
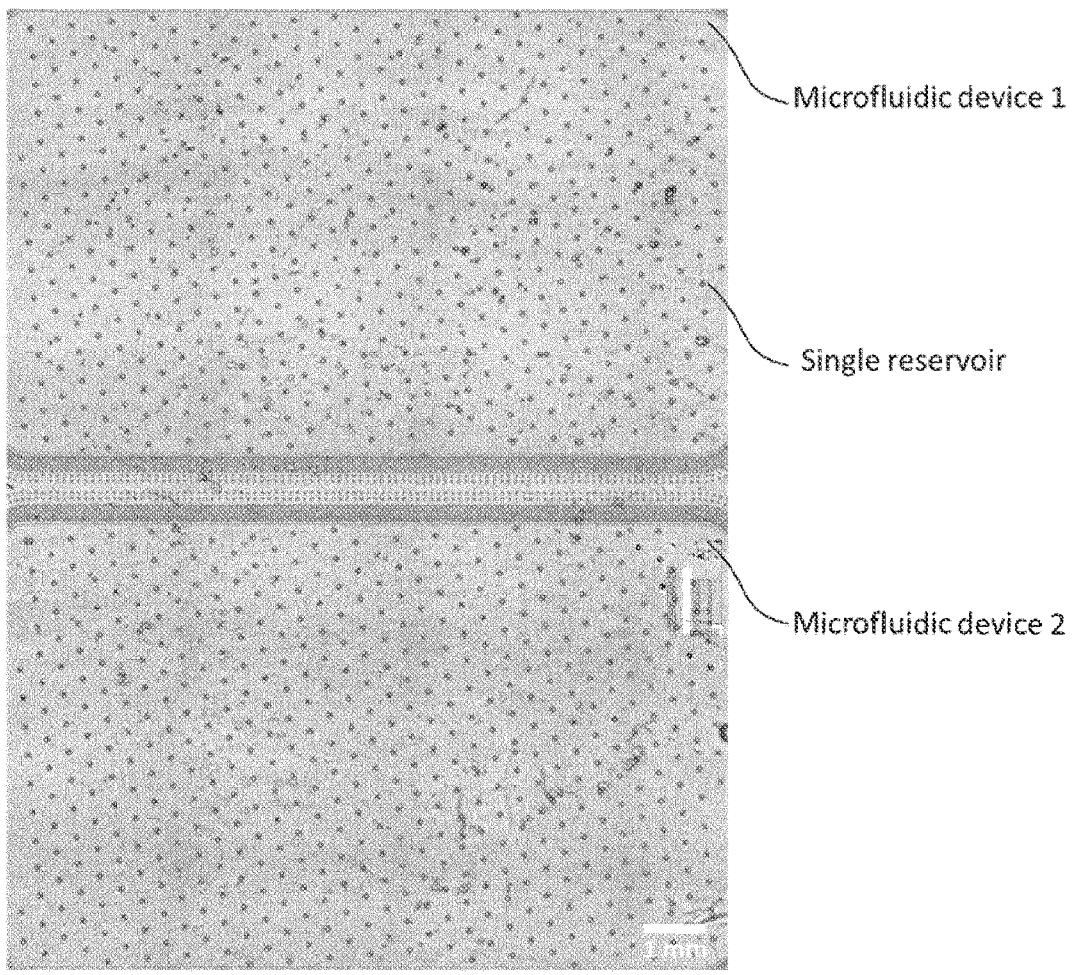
FIG. 9 shows an acquired image of the said microfluidic device containing 1060 buoyancy based capturing units. In this design two sequential chambers are used to increase the total amount of capture units.
Figure 10:
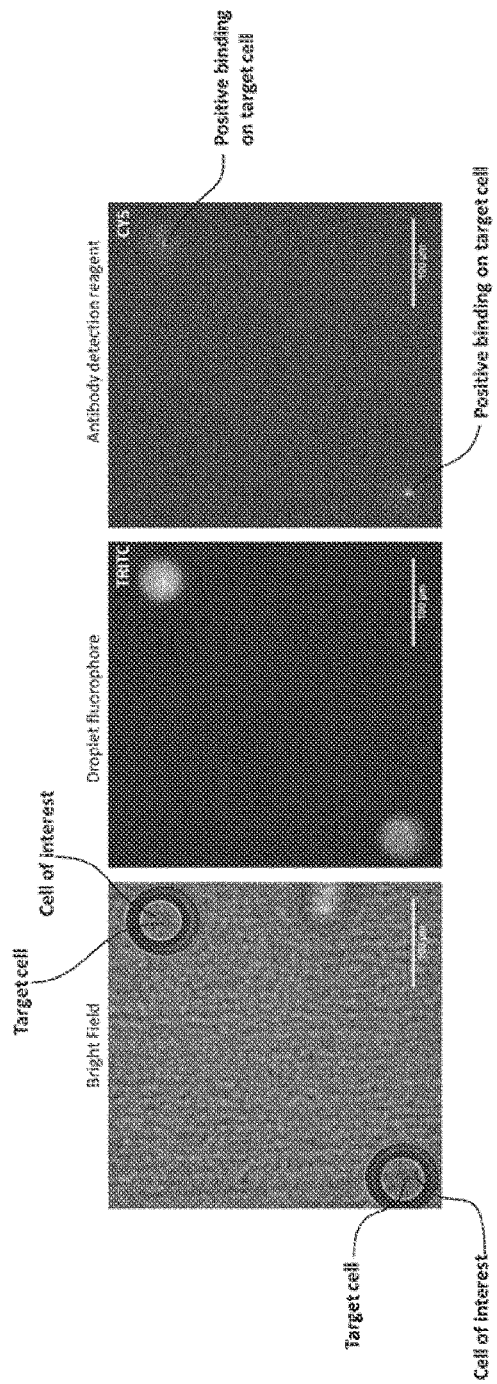
FIG. 10 shows some acquired images during a sorting, based on the binding of a target cell in the presence of the cell of interest. A. Bright filed acquisition of two capture units containing two sorted droplets loaded with one target cell and a cell of interest. B. Acquired image using the TRITC filter. A fluorescent molecule in used inside the droplet allowing the detection in the microfluidic device. C. Acquired image using the Cy5 filter showing the detection regent localized on the target cells.

The inventors have developed a process (see FIG. 8), wherein, in a microfluidic device comprising a chip, one single cell droplet comprising nucleic acids is specifically fused with a droplet comprising a reverse transcriptase and an oligonucleotide having a primer sequence. The nucleic acids are then reverse transcribed and ultimately barcoded during reverse transcription or afterwards. One advantage of this process is that little amounts of material are wasted, since one single cell droplet is specifically fused with one RT droplet. A further advantage is that unused barcodes are removed and that thus the signal to noise ratio is improved when the cDNA is sequenced.

Figure 7:
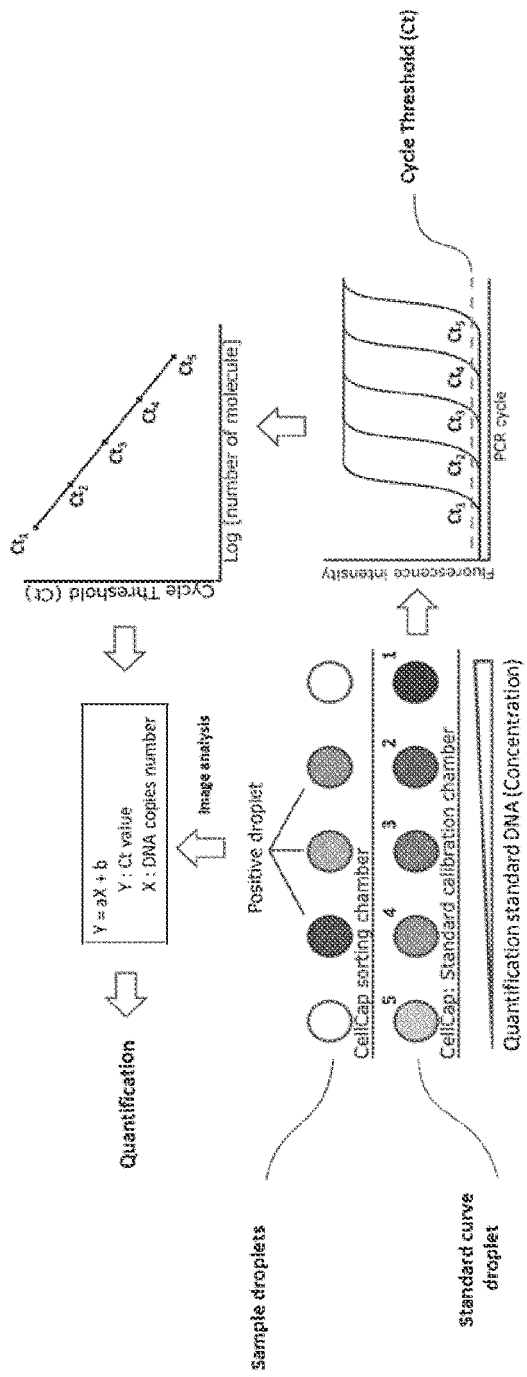
FIG. 7 shows an example of RT-PCR performed in a microfluidic device for combining phenotype and genotype information recovery. In this example a DNA intercalant or a Taq-man probe is added to the mix in addition of the RT-PCR reagents. For each cycle the number of copies increase exponentially to reach a plateau due to exhaustion of intercalating agent or probe. The intensity curve is then plotted in function of cycle, the Cycle Threshold (Ct) value is calculated. Ct value is then plotted in function of Log [number of molecule]. The number of molecule for a given sample is calculated from standard curves. Standard curve is generated from droplet containing a known amount of molecules, for which Ct is calculated as well. These Ct from standard sample are plot as a function of Log [number of molecule] graph, the equation of linear regression is then calculated and is used for the quantitative analysis of the sample droplet containing cells.

A further advantage is that the barcode itself could be used as primer to continue the single cell RT-PCR (see FIG. 7).

Accordingly, the present invention refers to a microfluidic process for barcoding single cell nucleic acids, said method comprises:

providing a microfluidic device comprising a chip comprising at least one microfluidic channel and a plurality of reservoirs, injecting into the inlet of the microfluidic channel a carrier fluid comprising a plurality of droplets of a first type dispersed in the carrier fluid, wherein the droplets of the first type are either single cell droplets or RT droplets, wherein at least some of the RT droplets comprise a reverse transcriptase and at least one oligonucleotide, and wherein at least some of the single cell droplets comprise one single cell, wherein said single cell comprises single cell nucleic acids, for a plurality of reservoirs, a first migration step, wherein at least one droplet of the first type among the plurality of droplets is moved into one reservoir of said plurality of reservoirs by buoyancy, injecting into the inlet of the microfluidic channel, a carrier fluid comprising a plurality of droplets of a second type dispersed in the carrier fluid, wherein the droplets of the second type are either single cell droplets or RT droplets, and wherein the droplets of the second type are RT droplets when the droplets of the first type are single cell droplets or the droplets of the second type are single cell droplets when the droplets of the first type are RT droplets, for a plurality of reservoirs, a second migration step, wherein, at least one part of at least one droplet of the second type enters into one reservoir of said plurality of reservoirs, for a plurality of reservoirs, fusing, in or at the edge of each reservoir, said at least one droplet of the first type with said at least one droplet of the second type, thereby resulting in a fused droplet, and further comprising the steps of:
  a) hybridizing, for each fused droplet, the at least some of the single cell nucleic acids with the at least one oligonucleotide in said fused droplet,
  b) reverse transcribing, in each fused droplet, at least some of the single cell nucleic acids present in said fused droplet, thereby resulting in single cell cDNA, and
  c) attaching at least one barcode sequence to the single cell cDNA obtained in step b), wherein said at least one barcode sequence encodes the identity of said single cell, or further comprising the steps of:
  a) hybridizing, for each fused droplet, at least some of single cell nucleic acids from at least one cell with the at least one oligonucleotide in said fused droplet, wherein said at least one oligonucleotide comprises at least one barcode sequence,
  b) reverse transcribing, in each fused droplet, at least some of the single cell nucleic acids present in said fused droplet, thereby resulting in barcoded single cell cDNA, wherein said at least one barcode sequence encodes the identity of said single cell.

Techniques to prepare and inject single cell droplets or RT droplets are well known to the skilled in the art and are further described in the section "preparation of droplets".

In some embodiments, the droplets of the first type are single cell droplets. In another set of embodiments, the droplets of the first type are RT droplets. Features relating to the single cell droplets and the RT droplets are described herein above in the previous sections, in particular, in the sections "droplets", "single cell", "reverse transcription" and "oligonucleotides". Accordingly, the description referring to "single cell droplets" or "RT droplets" provided in these sections are entirely applicable to this section called "microfluidic process for barcoding single cell nucleic acids".

The "at least one oligonucleotide" in context of the microfluidic processes of the invention comprises a primer sequence. The at least one oligonucleotide and primer sequence are defined herein above in the section "oligonucleotides".

In some embodiments, in the first migration step, the "at least one droplet of the first type" refers to 1, 2 or 3, preferably 1 or 2, more preferably 1 droplet of the first type.

Accordingly, in preferred embodiments, in the first migration step, for a plurality of reservoirs, one droplet of the first type is received in each reservoir by buoyancy.

"Buoyancy" generally refers to an upward force exerted by a fluid that opposes the weight of an immersed object. In context of the present invention, buoyancy refers to an upward force exerted by the carrier fluid that opposes the weight of a droplet immersed in said carrier fluid.

Accordingly, in some embodiments, the microfluidic device is oriented so that the plurality of reservoirs are above the channel and the at least one droplet of the first type enters in the above oriented reservoir by buoyancy. In this embodiment, the carrier fluid has a density that is higher than the density of the aqueous solution.

In some embodiments, the first migration step of the at least one droplet of a first type results in an occupancy of 50% to 100% of the plurality of reservoirs, such as 60% to 100%, 70% to 100%, 90% to 100%, for example 90%, 91%, 92%, 93%, 94%, 95%, 96%, 97%, 98%, 99% and 100%, preferably the migration step of the at least one droplet results in an occupancy of 90% to 100% of the plurality of reservoirs.

"Occupancy" herein refers to the number of reservoirs in comparison to the total number of reservoirs that are occupied with at least one droplet. Occupancy of 50%, for example, means that 50% of the reservoirs are occupied with at least one droplet.

In some embodiments, the first migration step of the at least one droplet of a first type results in a capturing efficiency of 10% to 100%, such 20% to 100%, 30% to 100%, 40% to 100%, 50% to 100%, 60% to 100%, 70% to 100%, 80% to 100%; 90% to 100% of the injected droplets, preferably 80% to 100%.

"Capturing efficiency" refers to the number of droplets in comparison to the total numbers of droplets that were injected into the inlet that are captured in reservoirs. Capturing efficiency of 50%, for example, means that 50% of the total number of the plurality of droplets that were provided are captured in reservoirs.

In some embodiments, in the second migration step of the at least one droplet of the second type refers to 1, 2 or 3, preferably 1 or 2, more preferably 1 droplet of the second type.

In the second migration step, the at least one droplet of a second type might either migrate completely into the reservoir or only partly, depending on the dimensions of the reservoir, the dimensions of the droplet of the second type and the dimensions of the droplet of the second type. Those dimensions are further defined in the section "droplets" and "microfluidic device".

Accordingly, in some embodiments, the at least one part of the at least one droplet of the second type refers to 50% to 100%, such as 60% to 100%, 65% to 100%, 70% to 100%, 75% to 100%, 80% to 100%, 85% to 100%, 90% to 100%, 95% to 100%, preferably 90% to 100% of the total volume of the at least one droplet of the second type.

Accordingly, in an alternative embodiment, the at least one part of the at least one droplet of the second type refers to 1 to 50%, 1% to 40%, 1% to 30%, such 2% to 30%, 5% to 30%, 10% to 30% of the total volume of the at least one droplet of the second type, preferably 10% to 30%.

In some embodiments, for a plurality of reservoirs, in the second migration step, at least one part of at least one droplet of a second type enters into one reservoir of said plurality of reservoirs due to buoyancy or the difference in surface energy, preferably the difference in surface energy.

In some embodiments, the second migration step of the at least one droplet of a second type results in an occupancy of 50 to 100% of the plurality of reservoirs, such as 60% to 100%, 70% to 100%, 90% to 100%, for example 90%, 91%, 92%, 93%, 94%, 95%, 96%, 97%, 98%, 99% and 100%, preferably the migration step of the at least one droplet of a second type results in an occupancy of 90% to 100% of the plurality of reservoirs.

In some embodiments, the second migration step of the at least one droplet of a second type results in a capturing efficiency of 10% to 100%, such 20% to 100%, 30% to 100%, 40% to 100%, 50% to 100%, 60% to 100%, 70% to 100%, 80% to 100%; 90% to 100% of the injected droplets, preferably 80% to 100%.

"Occupancy" and "Capturing efficiency" are as defined herein above.

In some embodiments, the droplets of the first type or the droplets of a second type might further comprise at least one particle of a second type, wherein said at least one particle of a second type is defined herein above in the section "single cells" and the particle is defined herein above in the section "oligonucleotides".

In some embodiments, the process further comprises a step of, for a plurality of reservoirs, performing for each reservoir a phenotypic assay on said at least one single cell.

As it will be understood by the skilled in the art, in some embodiments, performing a phenotypic assay might further require exposing the cell to reagents. Accordingly, in some embodiments, single cells are exposed to one or more reagents before, during, or after parameter measurement.

Accordingly, in some embodiments, the single cell droplets further comprise one or more reagents that are required for performing said single cell assay.

Accordingly, in some embodiments, the one or more reagents are integrated into the single cell droplet.

In some embodiments, the phenotypic assay is performed before the step of fusing the droplets. In some embodiments, the phenotypic assay is performed before lysing the cells. The phenotypic assay might further include the step of taking an image thereby mapping the phenotype of said at least one single cell for each reservoir. The "phenotypic assay" and the step of "taking an image" are as defined herein below in the section "process for genotyping single cells having a phenotype of interest".

In context of the process of the invention, the fusing step is performed for a plurality of reservoirs. As it will be understood by the skilled in the art, the fusion might be performed, for example, in selected areas of the chip, in particular if an electrical field is used for fusing the droplets.

Accordingly, in some embodiments related to the fusion step, the plurality of reservoirs might refer to some reservoirs of the plurality of reservoirs of the chip.

As it will be understood by the skilled in the art, in one example, based on the results of a phenotypic assay, the skilled in the art might select a plurality of reservoirs in which the RT droplets and the single cell droplets will be fused.

In some embodiments, in the fusing step, for each reservoir, at least one droplet of the first type is fused with at least a droplet of the second type using temperature, electrical field, demulsifier or ionic force, preferably, electrical field. The methods for fusing droplets are known to the skulled in the art and describe in, for example, WO 2010128157 A1.

In some embodiments, at least one droplet of the first type is fused with at least one droplet of the second type using electrical field, wherein the electric field is 10 kHz and 500V for at least 1 second, such as at least 2, 3, 4, 5, 6, 7, 8, 9, 10 seconds, typically 8 seconds.

In some embodiments, the fusion step results in a fusion efficiency of 80% to 100% between the droplets of the first type and the droplets of the second type, such as 85% to 100%, 90% to 100%, 92% to 100%; 93% to 100%, 94% to 100%, 95% to 100%, 96% to 100%, 97% to 100%, 98% to 100%, such as 98%, 99%, 100% between the droplets of the first type and the droplets of the second type, preferably 90% to 100%.

"Fusion efficiency between the droplets of the first type and the droplets of the second type" herein refers to number of events wherein the provision of one droplet of a first type and one droplet of a second type result in a fused droplet in comparison to the total number of events wherein one droplet of a first type and a second type are provided together.

In some embodiments, the process further comprises, for a plurality of reservoirs, the step of lysing the cell, for example, of the least one single cell droplet or the fused droplet, to release the nucleic acids from the single cell into the single cell droplet or the fused droplet.

Accordingly, in some embodiments of the processes of the invention the nucleic acids referred to in the hybridizing step, for example in the hybridizing step a), and in the reverse transcription step, for example the reverse transcription step b), are released nucleic acids.

The step of lysing the cells may either occur prior to the step of fusing the at least one droplet of the first type with said at least one droplet of the second type or after the step of fusing said droplets. Methods that may be used to lyse the cells are defined herein above in the section "cell lysis".

As it will be understood by the skilled in the art the method selected to lyse the cell may depend on the time point chosen for lysis, i.e. prior or after droplet fusion.

For example, enzymatic lysis or chemical lysis is typically used after the fusing step, because the components required for the enzymatic or chemical lysis are typically contained in the RT droplets.

In one preferred embodiment, the cell lysis does not destroy the droplets used in context of the invention.

Accordingly, in some embodiments, the RT droplets or plurality of RT droplets comprise a lysis composition, wherein the lysis composition is defined herein above in the section "Cell lysis".

In some embodiments, the method of the invention further comprises at least one purging step.

The "at least one purging step" in context of the invention refers to at least one, at least two, at least three, at least four purging steps.

For example, the device may typically be purged before injecting the plurality of droplets of the first type to remove residual air.

For example, the device may typically be purged after injecting the plurality of droplets of the first type to remove droplets of the first type that did not migrate into the plurality of reservoirs.

For example, the device may typically be purged after injecting the plurality of droplets of the second type to remove droplets of the second type that did not migrate, at least partly, into the plurality of reservoirs.

Step a) of the process of the invention refers to hybridizing, for each fused droplet, at least some of the single cell nucleic acids with the at least one oligonucleotide in said fused droplet.

"Hybridization" herein refers to a phenomenon in which a primer sequence, for example a primer sequence present in the at least one oligonucleotide, anneals to a complementary nucleic acid sequence of the nucleic acids, accordingly, as known by the skilled in the art, the temperature to be used for hybridization depends on the primer sequence and/or the RT enzyme used.

In one example, a hybridization step, for example, the hybridization step a) or b) is performed by incubating the droplets for example for 1 h at 55° C. to 60° C.

The reverse transcription of at least some of the single cell nucleic acids in step b) is further defined herein above in the section "reverse transcription".

In some embodiments, the at least one oligonucleotide comprises a primer sequence and at least one barcode sequence, wherein the "at least one oligonucleotide", the "at least one barcode sequence" and the "primer sequence" are defined herein above in the section "oligonucleotides".

In related embodiments, the reverse transcription of, for example step b), thus results in barcoded cDNA. According to the different embodiments described herein above said barcoded cDNA may be bound to a particle of a first type or not.

In some embodiments, the process of the invention further comprises the step of recovering the fused droplets at the outlet of the channel after the reverse transcription step.

"Recovering" herein refers to collecting the microfluidic droplets comprising cDNA or barcoded cDNA, produced by reverse transcription.

In some embodiments, recovering the fused droplets comprises a step of rotating the device around the X-Axis by 45° to 135°, preferably 90° and purging the device. The fused droplets can then be collected at the outlet.

In some embodiments, the step of recovering the fused droplets at the outlet of the channel after the reverse transcription step includes at least one washing step.

After washing the fused droplets, the downstream processing of the fused droplets may differ for droplets comprising barcoded cDNA in comparison to droplets comprising cDNA which is not barcoded.

The skilled in the art will understand that barcoded cDNA may processed differently, because barcoded single cell cDNAs obtained from one cell may be mixed with barcoded single cell cDNAs of another cell, since the cDNAs may be distinguished because of the barcode sequence. Contrary to this, cDNAs that are not barcoded can only be mixed when bound to a particle.

Accordingly, in some embodiments, the cDNA is not barcoded, in related embodiments, the cDNAs produced by the reverse transcription of step b) is recovered and then at least one barcode is attached in step c). After attaching a barcode in step c) the barcoded cDNA is further used for, typically, subsequent amplification and sequencing library preparation (see FIG. 11).

In some embodiments, the cDNA is barcoded, in related embodiments, the barcoded cDNAs produced by the reverse transcription of step b) are recovered and further used for, typically, subsequent amplification and sequencing library preparation.

Figure 11:
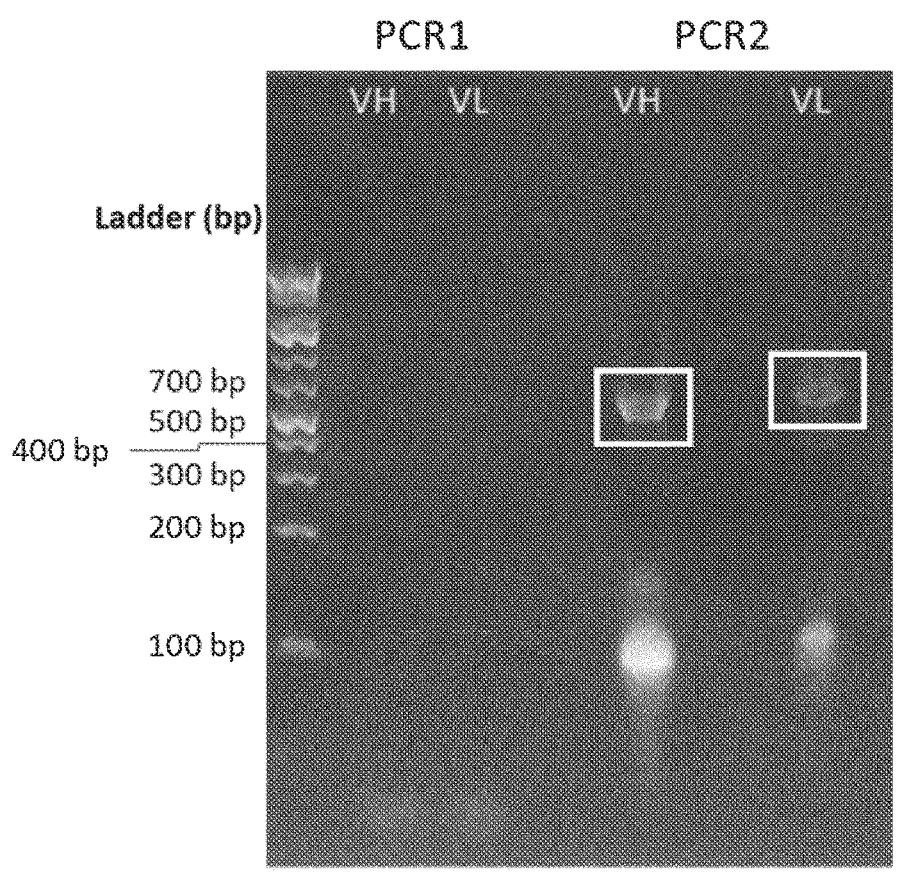
FIG. 11 shows a library preparation example and controls. After a two-step PCR reaction (PCR1 and PCR2), cDNA is amplified into Illumina based sequencing library. The PCR2 usually shows the product of amplification ~550 bp for VH and VL.

Subsequent amplification and sequencing library preparation is as defined herein above in the section "Amplifying and sequencing" (see FIG. 11).

Accordingly, in some embodiments, the process of the invention further comprises recovering barcoded single cell cDNAs produced by reverse transcription in at least some of the fused droplets.

More precisely, in related embodiments, recovering refers to collecting the microfluidic droplets comprising barcoded cDNA produced by reverse transcription, breaking the microfluidic droplets and separating the barcoded cDNA comprised in the aqueous composition from the oil phase of said microfluidic droplets.

Methods to isolate nucleic acids, in particular barcoded cDNA from droplets are known to the skilled in the art and comprise for example, collecting the microfluidic droplets and breaking the microfluidic droplets using typically perfluoro-octanol (v/v emulsion). Then incubating the emulsion obtained in the previous step until the aqueous and oil phase are separated. In one example, the aqueous phase is typically centrifuged for, for example, 10 min at 10,000 g at 4° C. and the supernatant comprising the cDNA is recovered.

In some embodiments, the process further comprises the step of removing unincorporated oligonucleotides.

"Removing unincorporated oligonucleotides" comprises contacting the aqueous composition comprising cDNA and eventually unincorporated oligonucleotides with a purification substrate wherein the purification substrate removes unincorporated oligonucleotides. As it will be understood by the skilled in the art, the cDNA submitted to the step of of removing unincorporated oligonucleotides is preferably barcoded cDNA.

In some embodiments, the purification substrate comprises beads or particles, which, optionally, form a column. In a further example, unincorporated oligonucleotides are removed by size selection using for example an acrylamide gel.

In some embodiments, the step of "removing unincorporated oligonucleotides" comprises contacting the aqueous composition comprising cDNA with an exonuclease to degrade the unincorporated oligonucleotides within the aqueous composition of the at least some of the droplets.

In related embodiments, the exonuclease degrades single stranded nucleic acid sequences from the aqueous compositions comprising the cDNA.

It will be understood by the skilled in the art that the cDNA, such as the barcoded cDNA, obtained, for example, in step b) or c), is typically present in form of a RNA/DNA complex and thus protected from said exonucleases.

In some embodiments, the cDNA comprises one or more nucleotide analogs, as defined herein above, facilitating purification of the cDNA sequences or molecules.

As it will be understood by the skilled in the art, in certain embodiments, purified cDNA does not comprise unincorporated oligonucleotides.

In some embodiments, the cDNA is further treated with RNAse A.

"RNAse A" is an endoribonuclease that specifically degrades single-stranded RNA at C and U residues.

In some embodiments, the RNAse A is at a concentration of 10 to 1000 m/A, preferably 50 to 200 µg/µL, for example at 100 µg/µL.

In some embodiments, the cDNA is further treated with Proteinase K.

"Proteinase K" is a broad-spectrum serine protease and digests proteins, preferentially after hydrophobic amino acids.

In some embodiments, the Proteinase K is at a concentration of 0.1 to 5 mg/mL, preferably 0.1 to 1 mg/mL, for example at 0.8 mg/mL.

Figure 5:
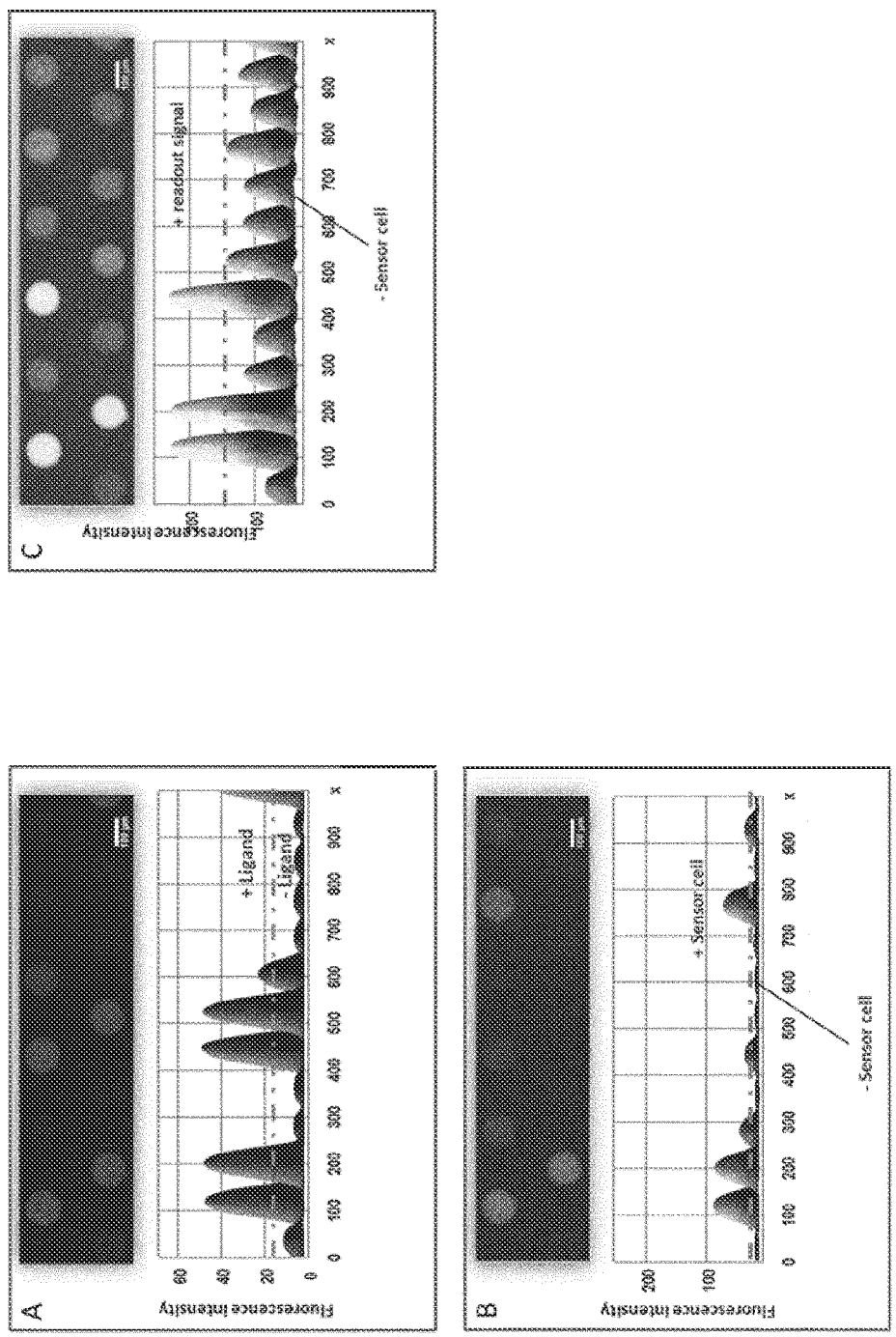
FIG. 5 shows a single cell droplet based phenotype assay for identification of agonistic activity of a ligand. The image acquisition is done with an epifluorescence-based microscope at 10× magnification. A. Different concentrations of fluorescent dye is added in function of ligand concentration to differentiate an emulsion containing an agonist (high fluorescent dye concentration), from an emulsion without agonist (low fluorescent dye concentration). B. The cells are labelled with a cell marker. After the fusion with the second droplet population, containing among other substrate for the detection of the intra cellular pathway activation detection and as well reagent for RT (+/−PCR), the cell is lysed leading to the diffusion of the cell marker leaks inside the droplet. A. combined with B. gives the information of the assay condition. C. Finally, the functional readout is given in a third colour showing in this case the recruitment of a downstream agonist induced intra-cellular signalling pathway activation. Above the threshold the droplet is considered as positive and match with the expectation given by conditions A.+B. This example highlight the feasibility to link a complex phenotype (downstream signalling intra cellular cascade activation) of a secreted antibody with its sequencing information.

The recovered cDNA is then further used for, typically, subsequent amplification and sequencing library preparation as defined herein above in the section "Amplifying and sequencing" (see also FIG. 5).

As explained herein above in the section "oligonucleotides", in embodiments where the at least one oligonucleotide is bound to at least one particle of a first type, reverse transcribing the nucleic acids present in the fused droplet results in single cell cDNA bound to the at least one particle of a first type in form of a RNA/DNA complex.

Furthermore, in embodiments where the at least one oligonucleotide does not contain a barcode sequence the cDNA obtained by reverse transcription and bound to said at least one particle of a first type is not barcoded.

Accordingly, in a related embodiment, recovering single cell cDNAs herein refers to breaking the microfluidic droplets and separating the single cell cDNA bound to at least one particle of a first type comprised in the aqueous composition from the oil phase of said microfluidic droplets.

Methods to break the microfluidic droplets are known to the skilled in the art and include typically the use of perfluoro-octanol (v/v emulsion).

The cDNA bound to a particle may be separated from the oil phase using methods known to the skilled in the art. For example, when the particle is a magnetic particle, the cDNA may be separated using a magnet. In another example, when the particle is a hydrogel particle, the cDNA may be separated by sedimentation.

Separating the cDNAs bound to at least one particle of a first type from the oil phase results in a pool comprising a plurality of particles of a first type, wherein to each particle cDNA of one cell is bound.

In related embodiments, for attaching the at least one barcode sequence, for example in step c), to the single cell cDNA, the process of the invention further comprises a step of distributing single cell cDNAs bound to the at least one particle of a first type into a plurality of reservoirs, wherein at least one particle of a first type, preferably one particle of a first type, to which the cDNA of one single cell is bound, is received in each reservoir. Such a reservoir may be, for example, a well of, typically, a well plate, such as a 96 well plate.

In some related embodiments, the process of the invention further comprises the step c) of attaching a barcode sequence to the single cell cDNA obtained in step b), wherein the at least one barcode sequence encodes the identity of said single cell.

The at least one barcode sequence is as defined herein above in the section "oligonucleotides". In a preferred embodiment, when the at least one barcode is attached after the transcription step, said at least one barcode sequence is preferably a single stranded nucleic acid. It will be understood by the skilled in the art that one barcode sequence, or more than one barcode sequence may be attached. When more than one barcode sequence is attached, individual barcode sequences attached to each other end up in one final barcode sequence. Those individual barcode sequences may be attached in subsequent cycles.

In some embodiments, the step c) of attaching a barcode sequence further comprises attaching a UMI sequence, wherein said UMI sequence is as defined herein above in the section "oligonucleotides".

Methods to attach barcode sequences or a UMI sequence are known to the skilled in the art and include, for example, the use of ligases and/or using annealing or a primer extension method.

In some embodiments, the step c) of attaching the barcode sequence may be followed by a washing step to remove barcodes that are not attached to the single cell cDNA.

In some embodiments, the process further comprises the step of removing unincorporated oligonucleotides. Methods to remove unincorporated oligonucleotides are further described herein above.

In embodiments, where the cDNA is attached to at least one particle of a first type, the process further comprises a step of releasing cDNA or barcoded cDNA from the at least one particle of a first type. Methods to release oligonucleotides are described herein above in the section "oligonucleotides" and apply mutatis mutandis to the release of cDNA since the cDNA is bound to the particle via said oligonucleotide.

Preferably, the step of releasing the cDNA occurs after attaching the barcode sequence in step c).

In some embodiments, the step c) of attaching the barcode sequence is followed by a step of recovering the barcoded cDNA.

Recovering the barcoded cDNA herein refers to collecting the barcoded cDNA.

The recovered barcoded cDNA is then further used for, typically, subsequent amplification and sequencing library preparation as defined herein above in the section "Amplification and sequencing" (see FIG. 11).

Furthermore, in some embodiments, the at least one oligonucleotide was introduced in the RT droplet without a particle or, optionally, released from said particle prior to reverse transcription.

Accordingly, it will be understood by the skilled in the art that these embodiments of the process of the invention result, after transcription, in cDNA that is not attached to a particle. Furthermore, in embodiments where the at least one oligonucleotide does not comprise a barcode sequence, said cDNA is not barcoded.

Accordingly, in related embodiments, the RT-droplets further comprise a polymer.

It will be understood by the skilled in the art, that accordingly, in some embodiments the fused droplets comprise said polymer.

In some embodiments, said polymer is in form of a solution.

In some embodiments, said polymer is selected from the group consisting of alginic acid, agarose, poly(ethylene glycol) diacrylate, or acrylamide-based gels, such as bis-acrylamide, polyacrylamide, streptavidine acrylamide, poly-N-isopropylacrylamide, or poly N-isopropylpolyacrylamide or mixtures thereof.

In a further embodiment, the polymer is functionalized to capture nucleic acids.

Methods to functionalize a polymer to capture nucleic acids are known to the skilled in the art and include, but are not limited to, streptavidine, Histidine-tags, biotin, calmodulin, SNAP-tag, Biotin, Acrydite.

In a related embodiment, the fused droplets are recovered as described herein above.

In related embodiments, the step of recovering fused droplets as defined herein above, further comprises the step of polymerizing the fused droplets.

For example, a hydrogel, such as alginic acid may be polymerized by the addition of calcium ions.

In other cases, polymerization initiators, also called cross-linker (such as ammonium persulfate and TEMED for acrylamide) may be added to a droplet.

It will be understood by the skilled in the art that, when polymerizing the fused droplets, the single cell cDNA produced in step b) is comprised in said polymerized droplets.

In some embodiments, polymerization is obtained by cross-linking.

In some embodiments the cross-linker is added to the fused droplets, for example, by diffusion.

In alternative embodiments, the RT-droplets comprise a cross-linker. It will be understood by the skilled in the art, that accordingly, in the same embodiments, also the fused droplets comprise said cross-linker.

In some embodiments, the cross-linker is activated for polymerization.

In particular, when the RT droplets comprise a cross-linker said cross-linker requires activation for polymerization.

In some embodiment, the cross-linker is activated by heat or UV.

In related embodiments, for attaching the barcode in step c) to the cDNA, the process of the invention further comprises a step of distributing polymerized droplets comprising single cell cDNAs in a plurality of reservoirs, wherein, preferably, one polymerized droplet is received in each reservoir. The reservoirs might be the well of, typically, a 96 well plate.

It is known to the skilled in the art that small nucleic acids, such as barcode sequences, as well as enzymes, such as ligases, may migrate into polymers as defined herein above.

Accordingly, the step c) of attaching the barcode sequence applies to cDNA comprised in said polymer in the same way as described herein above for cDNA attached to a particle. The step of attaching a barcode to the cDNA thus applies as defined herein above in the embodiments referring to cDNA attached to a particle.

Accordingly, the barcode may be attached either to the 3' or the 5' end.

In some embodiments, the step c) of attaching a barcode sequence further comprises attaching a UMI sequence as defined herein above.

In some embodiments, the step c) of attaching the barcode sequence is followed by a washing step to remove barcodes that were not attached to the cDNA.

In some embodiments, the process further comprises the step of removing unincorporated oligonucleotides. Removing unincorporated oligonucleotides is as defined herein above.

In some embodiments, the process further comprises a step of releasing the barcoded cDNA from the polymerized droplets. cDNA may be released from the polymerized droplets by simple diffusion, photocleaveage or electrophoresis.

Preferably, the step of releasing the cDNA occurs after attaching the barcode sequence in step c).

In some embodiments, the step c) of attaching the barcode sequence is followed by a step of recovering the barcoded cDNA. The recovered barcoded cDNA is then further used for, typically, subsequent amplification and sequencing library preparation as defined herein above in the section "Amplification and sequencing" (see FIG. 11).

Process for Genotyping Single Cells Having a Phenotype of Interest

"Genotyping" generally refers to the process of determining the nucleic acid sequence of an individual using biochemical methods. Genotyping in context of the present invention refers to determining the nucleic acid sequence of a single cell, in particular of a single cell of interest.

A "phenotype" usually refers to the composite of an organism's observable characteristics or traits, such as its morphology, development, biochemical or physiological properties. A phenotype results from the expression of an organism's genetic code, its genotype, as well as the influence of environmental factors and the interactions between the two. In context of the present invention, the phenotype of a single cell refers to the presence or absence of a specific characteristic, such as for example, the presence or absence of a specific antibody, or the presence or absence of a specific antigen or the presence or absence of a specific activity, which might be observed or is identified using, typically, a phenotypic assay.

Example of phenotype of interest is the detection of a biological response. Among these, detection of an immune response can be monitored by detecting ADCC (Antibody-Dependent Cell-Mediated Cytotoxicity) (3) induced by secretion of antigen-specific antibody (see FIG. 1).

Among biological events, detection of an immune response can be monitored by detecting Complement Dependent Cytotoxicity (CDC) (6) induced by secretion of antigen-specific antibody (see FIG. 2).

Among biological events, detection of a drug effect can be monitored by detecting ADC (Antibody Drug Conjugate) induced by secretion of antigen-specific antibody (see FIG. 3).

Among biological event, is included detection of drug function like agonistic/antagonistic antibody induced by secretion of antigen-specific antibody (see FIG. 4, 5).

Among biological event, is included detection of drug function like performing a competition assay (see FIG. 6).

Among biological event, is included detection of drug function like detection of cell mobility of a reporter cells mediated by the secretion of antibody (see FIG. 6). Such assay can be used to track the modification of behavior of a reporter cell inside the said droplet. A target cell (1) expressing the antigen of interest and loaded with a detectable label that is not released would be co-encapsulated with a IgG producing cell (2) and particles, as single cell droplet. The droplets would be incubated in conditions allowing antibody secretion. The secreted specific antibody would re-localize on the target cell. Meanwhile, a ligand/agonist is diffusing from the particle at similar kinetic than the IgG production and create a gradient of ligand. The reporter cell would migrate inside the particle in function of the ligand concentration (9). In case of blocking antibody (3), the reporter cell progression is altered. The migration can then be used for assessing the blocking/neutralising activity of and antibody.

Accordingly, in context of the process for genotyping single cells, single cells present in a plurality of reservoirs, for example, in the reservoirs of, typically, a 96 well plate or in the reservoirs of a microfluidic device, are first phenotyped and then genotyped. The inventors developed a process, wherein, based on the use of specific barcodes in combination with dyes it is possible, to link, after sequencing, the genetic sequence of a barcoded single cell cDNA with the phenotype observed for said single cell.

Accordingly, the present invention refers to a process for genotyping single cells having a phenotype of interest, said method comprises:
providing a plurality of reservoirs, and
a) for a plurality of reservoirs, providing, for each reservoir, at least one barcode sequence and at least one dye, wherein the at least one barcode sequence is associated with the color and the concentration of said at least one dye, and taking an image of the array thereby mapping the color and the intensity of the at least one dye for each reservoir; and
b) for a plurality of reservoirs, providing, for each reservoir, at least one single cell and performing for each reservoir a phenotypic assay on said at least one single cell, and taking an image thereby mapping the phenotype of said at least one single cell for each reservoir;
wherein step a) is performed before step b) or step b) is performed before step a); then
c) for a plurality of reservoirs, linking, for each reservoir, the phenotype of a single cell obtained in step b) to the color and the intensity of the at least one dye obtained in step a); and
for a plurality of reservoirs, reverse transcribing, for each reservoir, nucleic acids of said at least one single cell, to obtain single cell cDNA barcoded with said at least one barcode sequence which is associated with the color and concentration of the at least one dye; and
linking the genotype with the phenotype of said at least one single cell.

In one preferred embodiment, said process is a microfluidic process.

In some preferred embodiments, the plurality of reservoirs is comprised in a microfluidic device comprising at least one microfluidic channel. Accordingly, in one embodiment, the process is a microfluidic process comprising the step of providing a microfluidic device comprising a chip comprising at least one microfluidic channel and a plurality of reservoirs.

Accordingly, the present invention further refers to a microfluidic process for genotyping single cells having a phenotype of interest, said method comprises:
providing a microfluidic device comprising a chip comprising a plurality of reservoirs, and
a) for a plurality of reservoirs, providing, for each reservoir, at least one barcode sequence and at least one dye, wherein the at least one barcode sequence is associated with the color and the concentration of said at least one dye, and taking an image of the array thereby mapping the color and the intensity of the at least one dye for each reservoir; and
b) for a plurality of reservoirs, providing, for each reservoir, at least one single cell and performing for each reservoir a phenotypic assay on said at least one single cell, and taking an image thereby mapping the phenotype of said at least one single cell for each reservoir;
wherein step a) is performed before step b) or step b) is performed before step a); then
c) for a plurality of reservoirs, linking, for each reservoir, the phenotype of a single cell obtained in step b) to the color and the intensity of the at least one dye obtained in step a); and
for a plurality of reservoirs, reverse transcribing, for each reservoir, nucleic acids of said at least one single cell, to obtain single cell cDNA barcoded with said at least one barcode sequence which is associated with the color and concentration of the at least one dye; and
linking the genotype with the phenotype of said at least one single cell.

In context of the microfluidic process for genotyping single cells having a phenotype of interest, the "microfluidic process" and the "microfluidic device" are as defined herein above in the section "definitions".

The "barcode sequence" is as defined herein above in the section "oligonucleotide".

The "plurality of reservoirs" is as defined herein above in the section "microfluidic device".

In some embodiments, "at least one" in "at least one barcode sequence" and "at least one" in "at least one dye" refers to more than 1, more than 2, more than 3, such as 1, 2, 3, 4, 5, 6, 7, 8, 9, 10 barcode sequences and/or dyes, preferably 2, 3, 4, or 5 barcode sequences and/or dyes, more preferably, 2, 3 or 4 barcode sequences and/or dyes, even more preferably, 2 or 3 barcode sequences and/or dyes, for example, 2 barcode sequences and/or dyes.

In some embodiments, the dye refers to a fluorescent dye. The fluorescent dye is as defined herein above in the section "single cell".

In some preferred embodiments, the at least one barcode and the at least one dye are provided in one solution.

In some embodiments, the at least one barcode and the at least one dye are not linked to each other.

In some embodiments, the at least one barcode and the at least one dye are not covalently linked to each other.

In some embodiments, the at least one barcode and the at least one dye are not intentionally linked using non-covalent links.

"Intentionally" herein refers to the fact, that in some embodiments, the at least one barcode and the at least one dye are not exposed to specific conditions in order to induce a non-covalent link, i.e. they are not modified, using for example streptavidin and biotin, to be linked to each other using a non-covalent link. However, it will be understood by the skilled in the art, that due to the nature of the at least one dye and the nature of the nucleic acid of the at least one barcode sequence, in some cases, the at least one dye and the at least one barcode sequence may be associated to each other by non-covalent interactions. These "non-covalent interactions" include electrostatic effects, it-effects, van der Waals forces, and hydrophobic effects.

In some embodiments, the at least one barcode is provided together with at least one dye, wherein said at least one dye is provided at a known concentration.

In some embodiments, the concentration of the at least one dye is from 0.1 nM to 100 µM, such 1 nM to 50 µM, 1 nM to 30 µM, 1 µM to 50 µM, 1 µM to 30 µM, preferably 1 nM to 30 µM. It will be understood by the skilled in the art, that the concentration to be used depends on the nature of the at least one dye.

In some preferred embodiments, when two barcode sequences are provided, two dyes are provided, if three barcode sequences are provided, three dyes are provided.

It will be understood by the skilled in the art that, when at least one barcode sequence refers to one barcode sequence and at least one dye refers to one dye, the barcode sequence provided in a first reservoir differs from the barcode sequence provided in another reservoir and the dye provided together with the barcode sequence in the first reservoir differs from the dye provided together with the barcode sequence in another reservoir and/or the concentration of those dyes are different.

It will be further understood by the skilled in the art that, when at least one barcode sequence refers to two barcode sequences and, preferably, at least one dye refers to two dyes, then at least one of the two barcode sequences provided in a first reservoir differs from at least one of the two barcode sequences provided in the other reservoir, and at least one of the two dyes provided together with the two barcode sequences in the first reservoir differs from at least one dye of the two dyes provided together with the two barcode sequences in the other reservoir and/or the concentration of at least one of the two dyes provided together with the two barcode sequences in the first reservoir differs from the concentration of at least one dye of the two dyes provided together with the two barcode sequences in the other reservoir.

"Taking an image" in step a) herein refers to taking an image by any method known to the skilled in the art, for example, fluorescent microscopy, confocal microscopy or fluorescent imaging technique.

For further understanding step a) is exemplified herein below for two reservoirs (A and B) using two barcodes and two dyes in each reservoir without limiting step a) to this example. For example, barcode1 is provided together with, typically, Alexa fluor 405 (violet) in solution at a concentration of, typically, 10 µN/1. Barcode2 is provided together with, typically, Alexa fluor 532 (green) in solution at a concentration of, typically, 15 µN/1. Barcode1 is associated with Alexa fluor 405 at a concentration of 10 µM and Barcode2 is associated with Alexa fluor 532 at a concentration of 15 µM. When both barcodes, barcode 1 and barcode 2, are provided together in one reservoir (reservoir A), the colors and concentrations of the two dyes accompanying the barcodes are mixed. When taking, typically, a fluorescent microscopy image, the intensity and the color of the fluorescent signal will be recorded for each reservoir (including reservoir A). It is then possible, based on a reference scale, to conclude that the color and intensity recorded for the mixture of the two dyes present in reservoir A is associated with the combination of barcode 1 and 2.

When now, in another reservoir (called reservoir B), barcode 1 is provided together with Alexa fluor 405 at a concentration of 10 µM and Barcode 3 with, for example Alexa 546, at a concentration of 20 µM, reservoir B will have another color and intensity than reservoir A. Accordingly, based on the image taken in step a) it is possible, using a reference scale, to conclude that the color and intensity recorded for the mixture of dyes in reservoir B is associated with the combination of barcode 1 and 3.

Accordingly, taking an image of the array in step a) allows to map, for each reservoir of the plurality of reservoirs, the color and intensities of the at least one dye present in each reservoir. Furthermore, the color and intensity that is mapped for each reservoir is associated with the at least one barcode sequence present in those reservoirs. Accordingly, the skilled in the art can conclude from the image obtained in step a) for each reservoir of the plurality of reservoirs which at least one barcode sequence is provided in said reservoir.

The at least one barcode sequence and the at least one dye in step a) may be provided by any method known to the skilled in the art.

In some embodiments, for a plurality of reservoirs, the at least one barcode sequence is linked to the surface of each reservoir of the plurality of reservoirs.

In related embodiments, linking the at least one barcode sequence to the surface of a reservoir does not affect the at least one dye in solution. The phrase "does not affect the at least one dye in solution" means that the dye remains in solution.

Methods to link a nucleic acid, such as at least one barcode sequence, to a surface are known to the skilled in the art and are described for example in U.S. Pat. No. 5,412,087. Those methods are further described herein in above in the section "oligonucleotides" in context of linking at least one oligonucleotide to at least one particle of a first type.

Accordingly, in some embodiments, for the plurality of reservoirs, the at least one barcode sequence is covalently linked or non-covalently linked to the surface of the reservoir. "Non-covalently linked", "Covalently linked", "Streptavidin" are as defined herein above in the section "oligonucleotides".

In a preferred embodiment, the non-covalent bond is a streptavidin-biotin link.

Streptavidin-Biotin bonds are known to the skilled in the art. Accordingly, in one example, the surface of the reservoir is coated with, for example a hydrogel, as defined herein above in the section "oligonucleotide", said hydrogel may be functionalized with streptavidin and the at least one barcode sequence is functionalized with biotin.

In some embodiments, where the at least one barcode sequence refers to more than one barcode sequence, it will be understood by the skilled in the art, that, in some embodiments, the barcode sequences are linked sequentially to the surface of the reservoir. Accordingly, the first barcode sequence is linked to the surface of the reservoir as described herein above, then the second barcode sequence is attached to the first barcode sequence and eventually a third barcode sequence is attached to the second barcode sequence and so on, depending on the number of barcode sequences.

In an alternative embodiment, the barcode sequences are attached to each other resulting in one barcode sequence before linking said (at least one) barcode sequence to the surface of the reservoir.

In some further embodiments, the at least one barcode sequence is further attached to a UMI sequence, wherein said UMI sequence is as defined herein above in the section "oligonucleotides".

Methods to attach nucleic acids to each other, or to attach two barcode sequences or a UMI sequence to a barcode sequence are known to the skilled in the art and include, but are not limited to, the use of ligases and/or using annealing or a primer extension method.

Accordingly, in some embodiments, the solution in which the at least one barcode sequence and the at least one dye is provided further comprises a ligase. Examples of ligases are given herein above in the section "oligonucleotide".

Independent of the type of bond used to link the at least one barcode to the surface of a reservoir, the barcode sequence may further comprise at least one linker sequence.

In some embodiments, the barcode sequence is preferably linked to the surface using the 5' end or the 3' end, preferably the 5'end.

It will be understood by the skilled in the art, that, in some embodiments, where the at least one barcode sequence refers to more than one barcode sequence, the first barcode sequence (i.e the barcode sequence located at the 5' end or the 3' end, preferably the 5' end) which is linked to the surface of the well comprises at its 5' end or 3' end, preferably 5' end, at least one linker sequence.

In some embodiments, the "linker sequence" is a sequence with which the at least one barcode is optionally linked to the surface of the reservoir.

"Optionally linked herein" refers to the possibility that the at least one barcode sequence might be released, so that the at least one barcode sequence is preferably attached to the at least one primer sequence as further described herein below.

Preferably, the linker sequence is a cleavable linker sequence as defined herein above in the section "oligonucleotides".

Accordingly, in some embodiments, the process of the invention further comprises a step of releasing the at least one barcode sequence bound to the surface of the reservoir.

In some embodiments, when the method is performed in droplets as further described herein below, the at least one barcode sequence is released, in particular, into the at least one RT droplet.

In some embodiments, the at least one barcode sequence is released into at least one RT droplet by contacting the RT droplet with the surface of the reservoir.

In some embodiments, the RT droplet is contacted with the surface by wetting.

Accordingly, in some embodiments, the at least one barcode sequence is released into the at least one RT droplet by wetting.

"Wetting" herein refers to changing the surface energy of a liquid phase on a semi-solid or solid phase.

Furthermore, in some embodiments, the at least one barcode sequence linked to the surface of the reservoir is released from said surface prior to reverse transcribing the single cell nucleic acids.

Furthermore, in some embodiments, the at least one barcode sequence linked to the surface of the reservoir is released from said surface prior to lysing the at least one single cell.

When performed in droplets, in some embodiments, the at least one barcode sequence linked to the surface of the reservoir is released from said surface prior to fusing the at least one single cell droplet and the RT droplet.

In some embodiments, the at least one barcode can be released using any means, such as enzymes, nucleophilic/basic reagents, reducing agents, photo-irradiation, electrophilic/acidic reagents, organometallic and metal reagents, and oxidizing reagents.

In some embodiments, the at least one barcode can be released using enzymatic and/or photo cleavage. For example, an endonuclease may be used to cleave a linker sequence or any other sequence to release the at least one barcode sequence from the surface of the reservoir.

In a further embodiment, releasing the at least one barcode sequence refers to disrupting the bond, such as a streptavidin biotin bond, as described herein above in the section "oligonucleotides".

In some embodiments, the at least one barcode is released by enzymatic digestion of streptavidin.

It will be understood by the skilled in the art that components required to release the barcode sequence may be provided by any method known to the skilled in the art, either in each of the plurality of reservoirs or, when performed in droplets, for example in the RT droplets, so that, typically, the at least one barcode sequence is released when the RT droplet is contacted with the surface.

In step b) of the process, for the plurality of reservoirs, at least one single cell is provided in each reservoir.

"At least one single cell" is defined herein above in the section "single cell" and preferably refers to one single cell.

A "phenotypic assay" herein refers to a method which allows identifying the phenotype of a cell, more particularly the phenotype of a single cell. A "phenotype" is as defined herein above.

In some embodiments, the phenotypic assay is selected from detection of a DNA sequence; detection of an RNA sequence; detection of a molecule selected from the group consisting of a protein, carbohydrate, lipid, and any combination thereof; detection of a small molecule; detection of an activity; detection of an ion concentration; detection of an ion potential; and detection of a red-ox potential.

Depending on the phenotypic assay the at least one single cell may be assayed for selected parameters using any suitable assay method, which may be qualitative and/or quantitative. Suitable detection methods may include spectroscopic methods, electrical methods, hydrodynamic methods, imaging methods, and/or biological methods, among others, especially those adapted or adaptable to the analysis of the single cells. These methods may involve detection of single or multiple values, time-dependent or time-independent (e.g., steady-state or endpoint) values, and/or averaged or (temporally and/or spatially) distributed values, among others. These methods may measure and/or output analog and/or digital values.

"Spectroscopic methods" generally may include detection of any property of light (or a wavelike particle), particularly properties that are changed via interaction with a sample. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), diffraction, circular dichroism, and optical rotation, among others.

Suitable "photoluminescence methods" may include bioluminescence resonance energy transfer (BRET), fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), fluorescence activated cell sorting (FACS), and their phosphorescence and other analogs, among others.

As it will be understood by the skilled in the art, in some embodiments, performing a phenotypic assay might further require exposing the cell to reagents.

Accordingly, in some embodiments, single cells are exposed to one or more reagents before, during, or after parameter measurement.

In some embodiments, single cells are exposed to one or more reagents before they are provided in step b).

In some embodiments, the reagents referred to include, but are not limited to, chemical/biological cell modulators, detection/assay reagents, solvents, buffers, media, washing solutions.

"Chemical modulators or biological modulators" may include any reagent that is being tested for interaction with a cell. Interaction generally includes specific binding to particles and/or any detectable genotypic and/or phenotypic effect on particles (or modulators). Chemical/biological modulators may include ligands that interact with receptors (e.g., antagonists, agonists, hormones, etc.), ions, gases, carbohydrates, lipids, organics, polymers, proteins, small molecules, or nucleic acids, in particular siRNAs.

"Detection/assay reagents" may include stains, dyes, labels, enzymes, substrates, cofactors, and/or specific binding partners (SBPs), among others.

In some embodiments, "taking an image" in step b) refers to taking an image using any method known to the skilled in the art that is adapted to the phenotypic assay used, typically, a spectroscopic method. In particular, taking an image refers to taking an image using bright field microscopy or fluorescent microscopy with array or line cameras.

The skilled in the art knows how to adapt the phenotypic assay used with the reagents used and the technique to take an image.

Taking an image in step b) leads to mapping, for each reservoir, the phenotype of the single cell contained in each reservoir.

Accordingly, in step c) based on the image obtained in step a) and the image obtained in step b) the skilled in the art can link, for the plurality of reservoirs, the phenotype obtained in step b) in one reservoir to the color and the intensity of the at least one dye obtained in step a) for the same reservoir, wherein the color and the intensity of the at least one dye obtained in step a) is associated with the at least one barcode sequence provided in said same reservoir.

Accordingly, the skilled in the art can thus link in step c), for the plurality of reservoirs, the phenotype of the at least one single cell observed in one reservoir with the at least one barcode sequence provided in said same reservoir.

In some embodiments, the process further comprises, at least 1, at least 2, at least 3, at least 4, at least 5, at least 6, at least 7, at least 8, at least 9, at least 10, at least 11, such as 1, 2, 3, 4, 5, 6, 7, 8, 9, 10, 11 steps selected from the following steps:

at least one purging step, for a plurality of reservoirs, providing, for each reservoir, at least one oligonucleotide, wherein said at least one oligonucleotide comprises a primer sequence, for a plurality of reservoirs, attaching, for each reservoir, the at least one barcode sequence to the at at least one oligonucleotide, for a plurality of reservoirs, providing, for each reservoir, a lysis composition, for a plurality of reservoirs, lysing, for each reservoir, the at least one single cell, for a plurality of reservoirs, providing, for each reservoir, a reverse transcriptase and a reverse transcriptase composition, for a plurality of reservoirs, hybridizing, for each reservoir, the at least some of the single cell nucleic acids with the at least one barcoded oligonucleotide, recovering the barcoded single cell cDNA, removing unincorporated oligonucleotides from said barcoded cDNA, amplifying the barcoded single cell cDNA, sequencing the barcoded single cell cDNA.

These additional steps were described herein above in context of the "microfluidic process for barcoding single cell nucleic acids". Accordingly, it will be understood by the skilled in the art, that embodiments and features in the entire description relating to the above mentioned steps are applicable to these steps in their entirety.

For instance, the description referring to "at least one oligonucleotide" in the section "preparation of the droplets", "oligonucleotides", "reverse transcription" and "microfluidic process for barcoding single cell nucleic acids" is entirely applicable to the section called "process for genotyping single cells having a phenotype of interest". The description referring to "primer" or "primer sequence" in the section "definition", "reverse transcription", "oligonucleotides" and "microfluidic process for barcoding single cell nucleic acids" is entirely applicable to the section called "process for genotyping single cells having a phenotype of interest".

As it will be understood by the skilled in the art, the methods used for "attaching in each reservoir the at least one barcode sequence to the at least one oligonucleotide" are identical to the methods used for "attaching a barcode sequence to the single cell cDNA" as described in context of step c) in the process for barcoding single cell nucleic acids or in "attaching one at least one barcode sequence to a UMI sequence" or "attaching barcode sequences to one another" as described herein above. Accordingly, methods for attaching the at least one barcode sequence to the at least one oligonucleotide are known to the skilled in the art and include, typically, include, but are not limited to, the use of ligases and/or using annealing or a primer extension method. Examples of ligases are given herein above in the section "oligonucleotides". In some embodiments, the barcode sequence is preferably attached to the at least one oligonucleotide at the 5' end of the at least one oligonucleotide resulting in an oligonucleotide comprising from 5' to 3' a barcode sequence and a primer sequence. Accordingly, if the at least one oligonucleotide is linked to at least one particle, the at least one oligonucleotide is preferably released prior to attaching the at least one barcode sequence.

Furthermore, the description referring to a "lysis composition" in the section "definition", "cell lysis", "reverse transcription", "oligonucleotides" and "microfluidic process for barcoding single cell nucleic acids" is entirely applicable to the section called "process for genotyping single cells having a phenotype of interest". Similarly, description referring to the step of "lysing the at least one single cell" in the section "cell lysis", "reverse transcription", "oligonucleotides" and "microfluidic process for barcoding single cell nucleic acids" is entirely applicable to the section called "process for genotyping single cells having a phenotype of interest".

The description referring to "reverse transcriptase" and a "reverse transcriptase composition" or "the step of reverse transcribing" in the section "definition", "preparation of RT droplets", "reverse transcription", "oligonucleotides" and "microfluidic process for barcoding single cell nucleic acids" is entirely applicable to the section called "process for genotyping single cells having a phenotype of interest".

The description referring to the "hybridizing step" in the section "Definition" and "Microfluidic process for barcoding single cell nucleic acids" is entirely applicable to the section called "process for genotyping single cells having a phenotype of interest".

In some embodiments, recovering the barcoded single cell cDNA herein refers to isolating the barcoded cDNAs produced by reverse transcription from the reservoirs.

The description referring to the step of "removing unincorporated oligonucleotides" in the sections "Microfluidic process for barcoding single cell nucleic acids" is entirely applicable to the section called "process for genotyping single cells having a phenotype of interest".

The description referring to the step of "amplifying the barcoded single cell cDNA" and "sequencing the barcoded single cell cDNA" in the section "Amplifying and sequencing" is entirely applicable to the section called "process for genotyping single cells having a phenotype of interest".

It will be understood by the skilled in the art that the single cells in step b) comprise nucleic acids.

As described herein above, it will be understood by the skilled in the arts, the step of lysing the at least one single cell in one reservoir results in releasing nucleic acids from the single cell into said reservoir.

In some embodiments, the step of lysing the cells occurs prior to the transcription step. In some preferred embodiments, the step of lysing the cells occurs after step b) of performing a phenotypic assay.

According to the above, in some embodiment the microfluidic process for genotyping single cells having a phenotype of interest comprises:

providing a microfluidic device comprising a chip comprising a plurality of reservoirs, and 1. for a plurality of reservoirs, providing for each reservoir at least one barcode sequence and at least one dye, wherein the at least one barcode sequence is associated with the color and the concentration of said at least one dye, and taking an image of the array thereby mapping the color and the intensity of the dye for each reservoir; and 2. for a plurality of reservoirs, providing for each reservoir at least one single cell and performing for each reservoir a phenotypic assay on said at least one single cell, and taking an image thereby mapping the phenotype of said at least one single cell for each reservoir;

wherein step a) is performed before step b) or step b) is performed before step a); then 3. for a plurality of reservoirs, linking for each reservoir the phenotype obtained in step b) to the color and the intensity of the dye obtained in step a); and optionally, for a plurality of reservoirs, providing, for each reservoir, at least one oligonucleotide, wherein said at least one oligonucleotide comprises a primer sequence, optionally, for a plurality of reservoirs, attaching, for each reservoir, the at least one barcode sequence to the at at least one oligonucleotide, optionally, for a plurality of reservoirs, providing, for each reservoir, a lysis composition, optionally, for a plurality of reservoirs, lysing, for each reservoir, the at least one single cell, optionally, for a plurality of reservoirs, providing, for each reservoir, a reverse transcriptase and a reverse transcriptase composition, optionally, for a plurality of reservoirs, hybridizing, for each reservoir, the at least some of the single cell nucleic acids with the at least one barcoded oligonucleotide, for a plurality of reservoirs, reverse transcribing for each reservoir nucleic acids of said at least one single cell, to obtain single cell cDNA barcoded with said at least one barcode sequence which is associated with the color and concentration of the at least one dye;

optionally, recovering the barcoded single cell cDNA, optionally, removing unincorporated oligonucleotides from said barcoded cDNA, optionally, amplifying the barcoded single cell cDNA, optionally, sequencing the barcoded single cell cDNA, and linking the genotype with the phenotype of said at least one single cell.

In some embodiments, the process for genotyping single cells having a phenotype of interest is performed in droplets. Droplets are as defined herein above in the section "droplets".

Accordingly, the at least one single cell is provided in a droplet, referred to as single cell droplet. Description referring to "single cell droplets" in previous sections, such as "droplets", "single cell" and "microfluidic process for barcoding single cell nucleic acids" is entirely applicable to the section called "process for genotyping single cells having a phenotype of interest".

In related embodiments, the at least one oligonucleotide and the reverse transcriptase are provided in a droplet, herein referred to as a RT droplet. Accordingly, the description referring to "RT droplets" in proceeding sections, such as "definition", "droplets", "preparation of droplets", "single cell", "cell lysis", "reverse transcription", "oligonucleotides" and "microfluidic process for barcoding single cell nucleic acids", is entirely applicable to the section called "process for genotyping single cells having a phenotype of interest".

As it will be understood by the skilled in the art, in certain embodiments, either the RT droplet or the single cell droplet may be provided first, as described herein above in context of "microfluidic process for barcoding single cell nucleic acids". Accordingly, in some embodiments, the process comprises the steps of:

injecting into the inlet of the microfluidic channel a carrier fluid comprising a plurality of droplets of a first type dispersed in the carrier fluid, wherein the droplets of the first type are either single cell droplets or RT droplets, wherein at least some of the RT droplets comprise a reverse transcriptase and at least one oligonucleotide, and wherein at least some of the single cell droplets comprise one single cell, wherein said single cell comprises single cell nucleic acids, for a plurality of reservoirs, a first migration step, wherein at least one droplet of the first type among the plurality of droplets enters into one reservoir of said plurality of reservoirs, injecting into the inlet of the microfluidic channel, a carrier fluid comprising a plurality of droplets of a second type dispersed in the carrier fluid, wherein the droplets of the second type are either single cell droplets or RT droplets, and wherein the droplets of the second type are RT droplets when the droplets of the first type are single cell droplets or the droplets of the second type are single cell droplets when the droplets of the first type are RT droplets, for a plurality of reservoirs, a second migration step, wherein, at least one part of one droplet of the second type enters into one reservoir of said plurality of reservoirs.

The description referring to these steps in the section "Microfluidic process for barcoding single cell nucleic acids" is entirely applicable to the section called "Microfluidic process for genotyping single cells having a phenotype of interest".

In some embodiments, those steps may be performed before step b) of performing for each reservoir a phenotypic assay on said at least one single cell. As it will be understood by the skilled in the art the phenotypic assay of step b) as described herein above may be performed on single cells when present in droplets.

As it will be further understood by the skilled in the art, the phenotypic assay may be performed either when the single cell droplets are provided in the plurality of reservoirs or when both, the single cell droplets and the RT droplets are provided in the plurality of reservoirs.

In some embodiments, in the first migration step, the at least one droplet of the first type among the plurality of droplets enters into one reservoir of said plurality of reservoirs by buoyancy, hydrodynamic forces or by a physical field, preferably buoyancy.

As it will be further understood by the skilled in the art, when the process is performed in droplets, the method further comprises a step of for a plurality of reservoirs, fusing, in or at the edge of each reservoir, said at least one droplet of the first type with said at least one droplet of the second type, thereby resulting in a fused droplet.

In one preferred embodiment the fusing step is preferably performed after step b) of performing a phenotypic assay.

The description referring to the fusing step in previous sections, such as "microfluidic process for barcoding single cell nucleic acids", is entirely applicable to the section called "Microfluidic process for genotyping single cells having a phenotype of interest"

In some embodiments, when the process is performed in droplets, the at least one barcode sequence and the at least one dye are provided in each reservoir as defined herein above.

Accordingly, in some embodiments, after taking an image of the at least one dye in step a) the at least one barcode sequence is incorporated into RT droplets by, for example wetting as described herein above.

Alternatively, in some embodiments, the at least one barcode sequence and the at least one dye are provided together with the reverse transcriptase and the at least one oligonucleotide in the RT droplet of the plurality of RT droplets.

In related embodiments, the at least one barcode sequence is attached to the at least one oligonucleotide present in the RT droplet resulting in at least one barcoded oligonucleotide.

Methods to attach a barcode sequence to an oligonucleotide are described herein above. In some related embodiments, the RT droplet further comprises a ligase.

When the "process for genotyping single cells having a phenotype of interest" is performed in droplets the process further comprises after step c) the steps of:

hybridizing, for each fused droplet, at least some of single cell nucleic acids from at least one cell with the at least one barcoded oligonucleotide, reverse transcribing, in each fused droplet, at least some of the single cell nucleic acids present in said fused droplet, thereby resulting in barcoded single cell cDNA, wherein said barcode sequence encodes the identity of said single cell.

The description referring to the hybridizing and reverse transcribing step in previous sections, such as "Microfluidic process for barcoding single cell nucleic acids", is entirely applicable to the section called "Microfluidic process for genotyping single cells having a phenotype of interest".

When performed in droplets, the process of the invention further comprises the step of recovering the fused droplets at the outlet of the channel after the reverse transcription step. "Recovering the fused droplets" herein refers to collecting the microfluidic droplets comprising barcoded cDNA as described herein above in the section "Microfluidic process for barcoding single cell nucleic acids".

With regards to the "at least one oligonucleotide", in some embodiments the at least one oligonucleotide is linked to at least one particle of a first type. In some embodiments, the at least one oligonucleotide is introduced into the reservoir or the droplets, in particular into the RT droplets, by initially binding the at least one oligonucleotide to at least one particle of a first type.

Accordingly, description referring to at least one oligonucleotide linked to at least one particle of a first type in previous sections, such as in the section "oligonucleotide" and "Microfluidic process for barcoding single cell nucleic acids", is entirely applicable to the section called "Microfluidic process for genotyping single cells having a phenotype of interest".

Accordingly, in some embodiments, the at least one oligonucleotide is covalently linked or non-covalently linked to said at least one particle of a first type, wherein the "covalent link" or "non-covalent link" and "at least one particle of a first type" is defined herein above in the section "oligonucleotide".

Independent of the type of bond used to link the at least one type of oligonucleotide to the particle of a first type, the at least one type of oligonucleotide may further comprise at least one linker sequence, wherein said linker sequence is as defined herein above in the section "oligonucleotide".

Accordingly, in a further embodiment, the "at least one type of an oligonucleotide" or simply the "oligonucleotide" further comprises at least one linker sequence, said linker sequence is preferably comprised at the 5' end or the 3' end, more preferably the 5'end.

It will be thus understood by the skilled in the art that, in some embodiments, the at least one oligonucleotide is bound to the particle of a first type via 3' end or the 5' end, preferably the 5' end.

In some embodiments, the process of the invention further comprises a step of releasing the at least one oligonucleotide bound to the at least one particle of a first type from said particle after it has been incorporated into the reservoir or the RT droplet.

Furthermore, in some embodiments, the at least one oligonucleotide initially bound to the at least one particle of a first type is released from said at least one particle of a first type prior to reverse transcribing the single cell nucleic acids.

Furthermore, in some embodiments, the at least one oligonucleotide initially bound to the at least one particle of a first type is released from said at least one particle of a first type prior to or after attaching the at least one barcode.

The step of releasing the at least one oligonucleotide may occur prior or after fusing the single cell and the RT droplets; preferably, prior to fusing the droplets.

The step of releasing the at least one oligonucleotide may occur after lysing the single cell but before reverse transcribing the single cell nucleic acids.

The skilled in the art will understand that the number of oligonucleotides present in one reservoir or droplet will be adapted to the number of different nucleic acids, in particular to the number of RNAs, that are to be transcribed and barcoded from one single cell. The number of oligonucleotides in a reservoir or droplet is adapted in the same manner as described for adaption of oligonucleotides in RT droplets in the section "oligonucleotides". Accordingly, "at least one" in the wording "at least one oligonucleotide" refers to the number of different oligonucleotides present in one reservoir or droplet, wherein one oligonucleotide of the at least one oligonucleotide differs from another oligonucleotide by its primer sequence. "At least one" in the wording "at least one oligonucleotide" is as defined in the section "oligonucleotides".

The concentration of the at least one oligonucleotide is as defined herein above in the section "oligonucleotides".

The concentration of the at least one oligonucleotide is at least 10 nM, preferably at least 100 nM.

Throughout the instant application, the term "and/or" is a grammatical conjunction that is to be interpreted as encompassing that one or more of the cases it connects may occur. For example, the wording "error detection and/or correction" in the phrase "the sequences allow for error detection and/or correction" indicates that the sequences may allow for error detection and the sequence may allow for error correction or the sequences may allow for error detection or the sequence may allow for error correction.

As used in this specification and the appended claims, the singular forms "a," "an" and "the" include plural references, such as a plurality of the object referred to, unless the content clearly dictates otherwise.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

In the entire description, features described in one section are entirely applicable to other sections of the instant description. Accordingly, the invention further contains combinations of embodiments described in the different sections of the description.

The invention claimed is:

1. A process for genotyping single cells having a phenotype of interest comprising:
   providing a plurality of reservoirs, and
   a) for the plurality of reservoirs, providing, for each reservoir, at least one barcode sequence and at least one dye, wherein the at least one barcode sequence is associated with the color and the concentration of said at least one dye, and taking an image of the array thereby mapping the color and the intensity of the at least one dye for each reservoir; and
   b) for the plurality of reservoirs, providing, for each reservoir, a single cell and performing for each reservoir a phenotypic assay on said single cell, and taking an image thereby mapping the phenotype of said single cell for each reservoir;

wherein step a) is performed before step b) or step b) is performed before step a);
then
c) for the plurality of reservoirs, linking, for each reservoir, the phenotype of a single cell obtained in step b) to the color and the intensity of the at least one dye obtained in step a); and
for the plurality of reservoirs, reverse transcribing, for each reservoir, nucleic acids of said single cell, to obtain single cell cDNA barcoded with said at least one barcode sequence which is associated with the color and concentration of the at least one dye; and
linking the genotype with the phenotype of said single cell;
wherein the process is a microfluidic process comprising a step of providing a microfluidic device comprising a chip comprising at least one microfluidic channel and a plurality of reservoirs;
wherein, for each reservoir, the single cell is provided in a single cell droplet.

2. The microfluidic process according to claim 1, wherein said process further comprises at least one step selected from the group consisting of:
at least one purging step,
for a plurality of reservoirs, providing, for each reservoir, at least one oligonucleotide, wherein said at least one oligonucleotide comprises a primer sequence,
for a plurality of reservoirs, attaching, for each reservoir, the at least one barcode sequence to the at least one oligonucleotide,
for a plurality of reservoirs, providing, for each reservoir, a lysis composition,
for a plurality of reservoirs, lysing, for each reservoir, the single cell,
for a plurality of reservoirs, providing, for each reservoir, a reverse transcriptase and a reverse transcriptase composition,
for a plurality of reservoirs, hybridizing, for each reservoir, the at least some of the single cell nucleic acids with the at least one barcoded oligonucleotide,
recovering the barcoded single cell cDNA,
removing unincorporated oligonucleotides from said barcoded cDNA,
amplifying the barcoded single cell cDNA,
sequencing the barcoded single cell cDNA.

3. The microfluidic process according to claim 1 or 2, wherein, for each reservoir, the reverse transcriptase, the reverse transcriptase composition and the at least one oligonucleotide are provided in a RT droplet.

4. The microfluidic process according to claim 1 or 2, wherein, for the plurality of reservoirs, the at least one barcode sequence is linked to the surface of each reservoir of the plurality of reservoirs.

5. The microfluidic process according to claim 4, wherein the at least one barcode sequence is released prior to transcription.

* * * * *